(12) United States Patent
Hochschuler et al.

(10) Patent No.: US 8,603,141 B2
(45) Date of Patent: Dec. 10, 2013

(54) INTERVERTEBRAL IMPLANT DEVICES AND METHODS FOR INSERTION THEREOF

(75) Inventors: Stephen H. Hochschuler, Paradise Valley, AZ (US); Ali Araghi, Phoenix, AZ (US); Thomas S. Kilpela, Marquette, MI (US); Jeffrey A. Hoffman, Anchorage, AK (US); Michael R. Jackson, Hancock, MI (US); Russell M. Pietila, Hancock, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 154 days.

(21) Appl. No.: 12/945,785

(22) Filed: Nov. 12, 2010

(65) Prior Publication Data

US 2011/0118788 A1  May 19, 2011

Related U.S. Application Data

(63) Continuation-in-part of application No. 12/234,557, filed on Sep. 19, 2008, now Pat. No. 8,308,767.

(60) Provisional application No. 61/260,551, filed on Nov. 12, 2009, provisional application No. 60/973,659, filed on Sep. 19, 2007.

(51) Int. Cl.
*A61B 17/70* (2006.01)

(52) U.S. Cl.
USPC ........... 606/246; 606/248; 606/252; 606/253; 606/278

(58) Field of Classification Search
USPC .......................................... 606/248–253, 278
See application file for complete search history.

(56) References Cited

U.S. PATENT DOCUMENTS

| | | | | |
|---|---|---|---|---|
| 5,275,600 A * | 1/1994 | Allard et al. | | 606/252 |
| 6,096,039 A * | 8/2000 | Stoltenberg et al. | | 606/252 |
| 6,139,548 A * | 10/2000 | Errico | | 606/252 |
| 6,736,817 B2 * | 5/2004 | Troxell et al. | | 606/252 |
| 7,842,071 B2 * | 11/2010 | Hawkes | | 606/252 |
| 7,918,876 B2 * | 4/2011 | Mueller et al. | | 606/251 |
| 7,988,708 B2 * | 8/2011 | Yeh | | 606/248 |
| 8,025,678 B2 * | 9/2011 | Reynolds et al. | | 606/249 |
| 8,262,701 B2 * | 9/2012 | Rathbun et al. | | 606/250 |
| 8,308,767 B2 * | 11/2012 | Hochschuler et al. | | 606/246 |
| 2005/0107789 A1 * | 5/2005 | Sweeney | | 606/61 |
| 2008/0015588 A1 * | 1/2008 | Hawkes | | 606/64 |
| 2008/0306538 A1 * | 12/2008 | Moore et al. | | 606/250 |
| 2010/0106190 A1 * | 4/2010 | Linares | | 606/249 |

* cited by examiner

*Primary Examiner* — Jerry Cumberledge
(74) *Attorney, Agent, or Firm* — Fitch, Even, Tabin & Flannery LLP

(57) ABSTRACT

An implant device includes a pair of hook devices and an elongate guide device. The hook devices are configured to be disposed between and engage adjacent vertebral bodies. The elongate guide device is connected to the hook devices and allows for relative movement of at least one of the hook devices to adjust for the geometries of the vertebral surfaces to be engaged by the hook devices.

24 Claims, 34 Drawing Sheets

INTERVERTEBRAL IMPLANT DEVICES AND METHODS FOR INSERTION THEREOF

CROSS REFERENCE TO RELATED APPLICATIONS

This application claims the benefit of U.S. Provisional Application No. 61/260,551, filed Nov. 12, 2009, and is a continuation-in-part of U.S. patent application Ser. No. 12/234,557, filed Sep. 19, 2008, now U.S. Pat. No. 8,308,767, and claims the benefit of the filing date of U.S. Provisional Application No. 60/973,659, filed Sep. 19, 2007, all of which are hereby incorporated by reference in their entirety herein.

FIELD OF THE INVENTION

The present invention relates generally to a spinal stabilization system and, more particularly, a spinal stabilization system for distracting and limiting reduction of the intervertebral spacing between adjacent vertebrae.

BACKGROUND

This invention pertains to medical implantable devices and particularly to spinal implants. Various devices for internal fixation of bone segments in the human or animal body are known in the art. The most common types of spinal implant systems are hook and rod systems and pedicle screw systems which provides a means of gripping a spinal segment. These implant systems are often used in conjunction with another implant device to be positioned in an intervertebral disc space between the ends plates of adjacent vertebral bodies for fixing the relative locations of the end plates. However, both hook and rod and pedicle screw systems have limitations and are not appropriate for all types of spinal disorders.

Conventional hook and rod systems comprise a series of hooks and an elongate rod. Typically, the hooks are positioned against lamina which are not adjacent one another to decompress or compress a section of the spine. Further, the hooks are positioned before being connected to the connecting rod, requiring the surgeon to place each individual hook before attempting to mount the connecting rod onto the hooks.

A conventional pedicle screw system comprises a pedicle screw and a rod-receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

The implantation of pedicle screw systems are intricate, time consuming, and invasive into the spine of the patient. Typically, a series of pedicle screws must be carefully placed precisely in the narrow pedicle region of the spine. These pedicle screws are then fitted with rod receiving devices which are then in turn fitted with distraction rods. The system of screws and rods creates an intricate system for supporting the spine that takes considerable effort.

The placement of the hooks, screws and rods is time consuming because the components must be positioned through trial and error with repeated adjustment of position of the components until final proper positioning of all the components of the entire system is achieved simultaneously. In addition, the implantation of pedicle screw systems is highly invasive because screws must be deeply driven into the pedicle region of the spine within close proximity of the nerves of the spinal cord or spinal nerves branching off of the spinal cord. Further, the rod is positioned out from within the intervertebral space, resulting in a larger overall implant assembly being implanted in the spinal area.

Other implant devices which are generally less time consuming to install and which are contained within the intervertebral space between adjacent vertebral bodies are known. Generally, these implant devices include a reduced profile orientation to assist in implantation of the implant device. The implant devices further include a predetermined enlarged profile orientation, such that as the implant device is shifted from the reduced profile orientation to the enlarged profile orientation the implant device engages the opposing laminar surfaces and separates the laminar surfaces to provide a desired, predetermined distraction distance. However, unlike the pedicle screw and rod systems, these implant devices are not configured to variably distract the engaged laminar surfaces to adjust for the geometries of an individual spine. As such, multiple implant devices may need to be inserted and removed to ensure that the geometries of spine and the desired distraction distance are provided for.

SUMMARY OF THE INVENTION

In accordance with one aspect of the invention, a spinal implant assembly is provided which allows for in situ manipulation of an implant device to adjust for the geometries of the vertebral surfaces to be engaged by the implant device. The spinal implant assembly includes an upper hook portion and a lower hook portion each having seat portions configured to engage facing surfaces of adjacent vertebral bodies. An elongate guide device extends between and connects the hook portions. In one form, a multi-axial pivot connection between one of the hook portions and the elongate guide device allows the seat portions to be oriented to securely engage the vertebral surfaces despite variations in their relative positions, such as in different locations along the spine or in different patients. A slide connection between the other hook portion and the elongate guide device allows the adjacent vertebrae to be distracted with the seats securely engaged against the vertebral surfaces.

In another form, a pivot connection is provided between one of the hook portions or members and the elongate guide device with the other hook member having the slide connection to the elongate guide device. The one hook member is pivotable to a compact insertion orientation so that its longitudinal axis extends generally transverse to the longitudinal axis of the elongate guide device, and then pivoted from the compact insertion orientation to a compact implanted orientation so that hook longitudinal axis is generally parallel to the guide device longitudinal axis. The other hook member is then slideable so that the hook members are spaced from one another in an extended implantation orientation.

In accordance with another aspect of the invention, a spinal implant assembly is provided that has a reduced profile extending out from within the intervertebral space, more particularly the space between the laminae of adjacent vertebrae. In this regard, the spinal implant assembly includes a pair of hook devices for engaging the laminar surfaces. The hook devices each include a pair of arms extending on either side of the laminar surface and a seat between the arms configured to engage the laminar surface. An elongate guide device is connected to each of the hook devices and allows for at least one of the hook devices to translate along the elongate guide device to distract the laminar surfaces. The elongate guide device has a longitudinal axis that extends through the seat or one of the arms of each of the first and second hook devices. In this manner, the elongate guide device extends generally axially in the axial space between the laminae of the adjacent vertebrae.

The configuration of prior art laminar distraction assemblies either allowed for the laminar surfaces to be distracted to various distances from each other while having the guide device for this purpose arranged outside the intervertebral space or axially extending envelope between the laminae of the adjacent vertebrae or substantially maintained the structure of the assembly within the laminar envelope but did not allow for variable distraction of the laminar surfaces from each other. By contrast, the above described spinal implant assembly has the hook and guide devices thereof configured and arranged to provide both a compact configuration for substantially fitting in within the laminar envelope while also allow for variable distraction of the laminar surfaces from each other.

In accordance with another aspect of the invention, a spinal implant assembly is provided which includes a releasable connection which allows for easy removal and replacement of a hook device. In this regard, the spinal implant assembly includes a pair of hook devices connected to an elongate guide device. A releasable connection between one of the hook devices and the elongate guide device allows the one hook device to be pulled off the elongate guide device for removal therefrom and to be pushed onto the elongate guide device to connect the one hook device onto the elongate guide device. In one form, the releasable connection is a snap-fit connection between the one hook device and the elongate guide device. The releasable connection advantageously allows a surgeon to easily assemble the hook device on the elongate guide device or select between different sizes of the hook device for placement on the elongate guide device. With the snap-fit connection, the use of tools is completely avoided for this purpose.

In accordance with another aspect of the invention, a method of implanting a spinal device is provided that allows for engaging and distracting adjacent vertebral bodies without requiring the adjacent vertebral bodies to be distracted prior to engagement. In this regard, the method includes positioning an implant device so that hook members of the implant device engage adjacent vertebral bodies. One of the hook members can then be pivoted about a guide portion of the implant device so that a seat portion of the one hook member is shifted into engagement with the vertebral body engaged by the one hook member. With the one hook member seat engaged with the vertebral body, the other hook member can then be translated along the guide portion away from the one hook member to distract the adjacent vertebral bodies. In one form, the method includes shifting the other hook member as the one hook member is pivoted so that the other hook member seat portion engages the vertebral body. The method advantageously allows a surgeon to insert hook members of an implant device into engagement with vertebral bodies, to then pivot one of the hook members so that the seat portions of the hook members are in engagement with the vertebral bodies, and then to distract the vertebral bodies without having to pre-distract the vertebral bodies to fit the hook members therebetween. In addition, shifting the other hook member during pivoting of the one hook member allows a surgeon to orient the seat portions to engage both vertebral bodies at one time instead of having to position each hook member individually for this purpose.

In another form, pivoting the one hook member includes pivoting the one hook member about multiple axes to adjust the orientation of the seats of the hook members to the geometry of the vertebral bodies engaged thereby. With multi-axial pivoting the one hook member to adjust for vertebral surface geometries, the implant device can advantageously engage the adjacent vertebrae more securely despite variations in their structures along the spine and between different patients.

DETAILED DESCRIPTION

Figure 2:
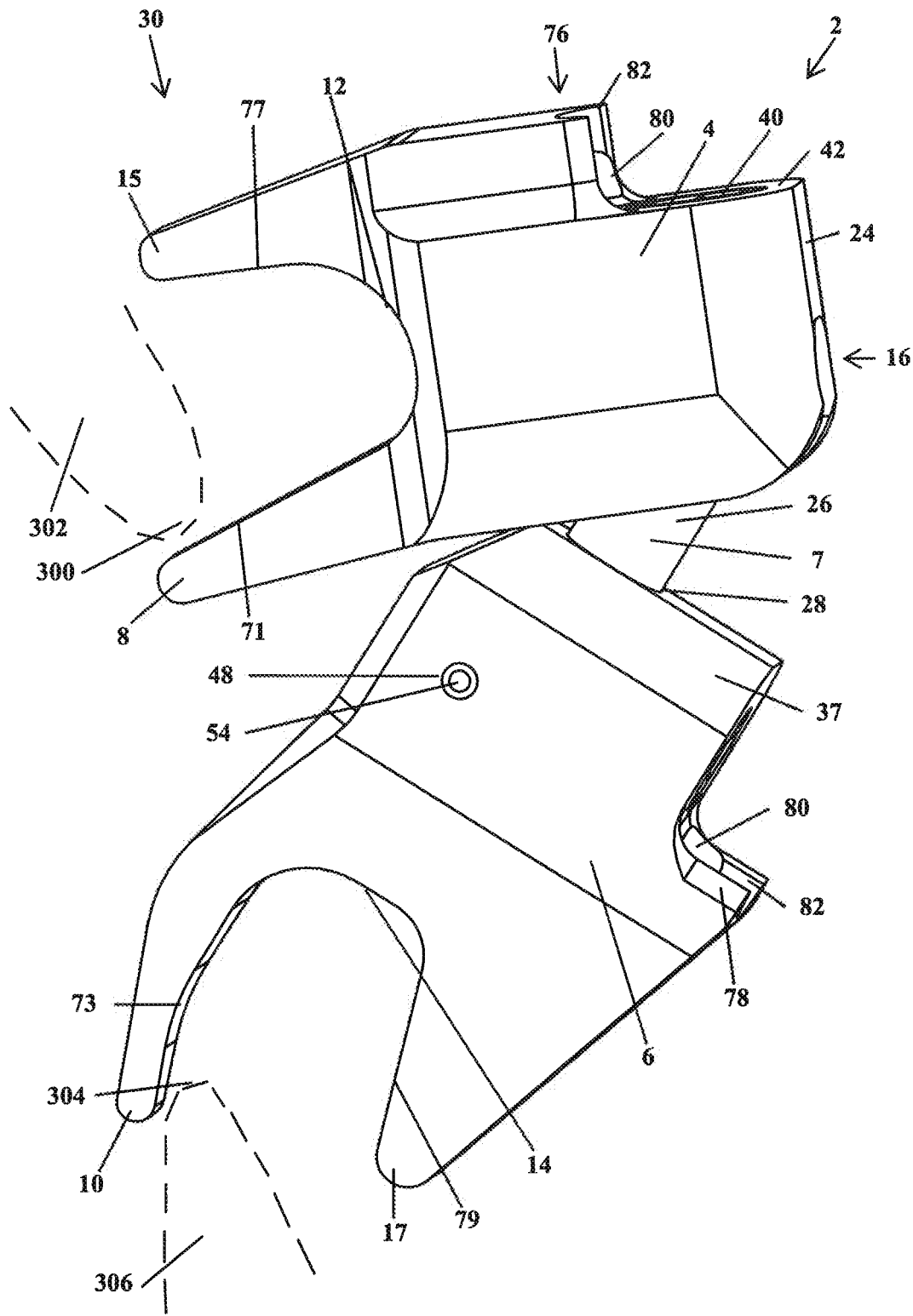
FIG. 2 is a side elevational view of the implant device of FIG. 1 showing the superior and inferior hook members in the compact insertion orientation.
Figure 3:
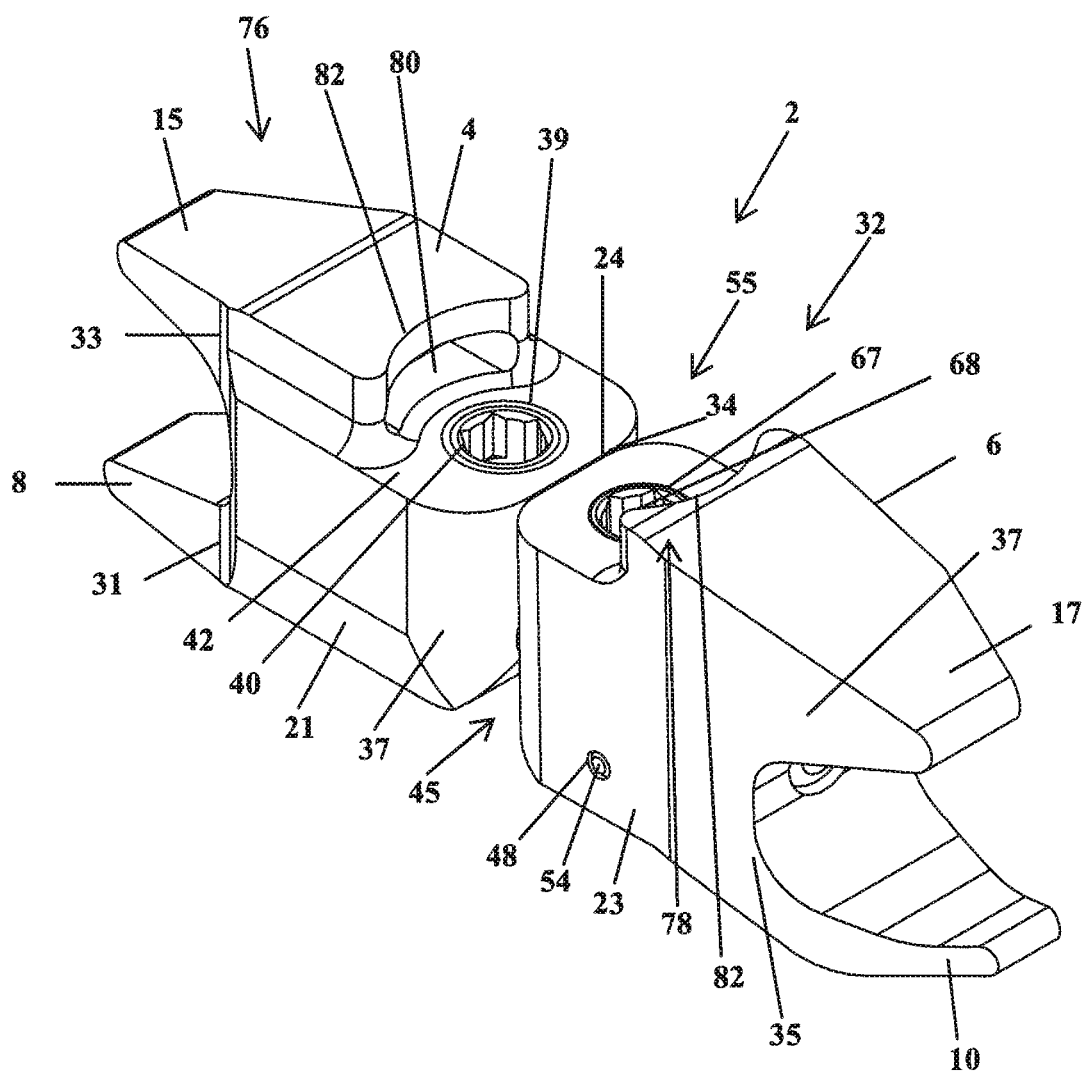
FIG. 3 is a perspective view of the implant device of FIG. 1 showing the superior and inferior hook members in the compact implanted orientation.
Figure 4:
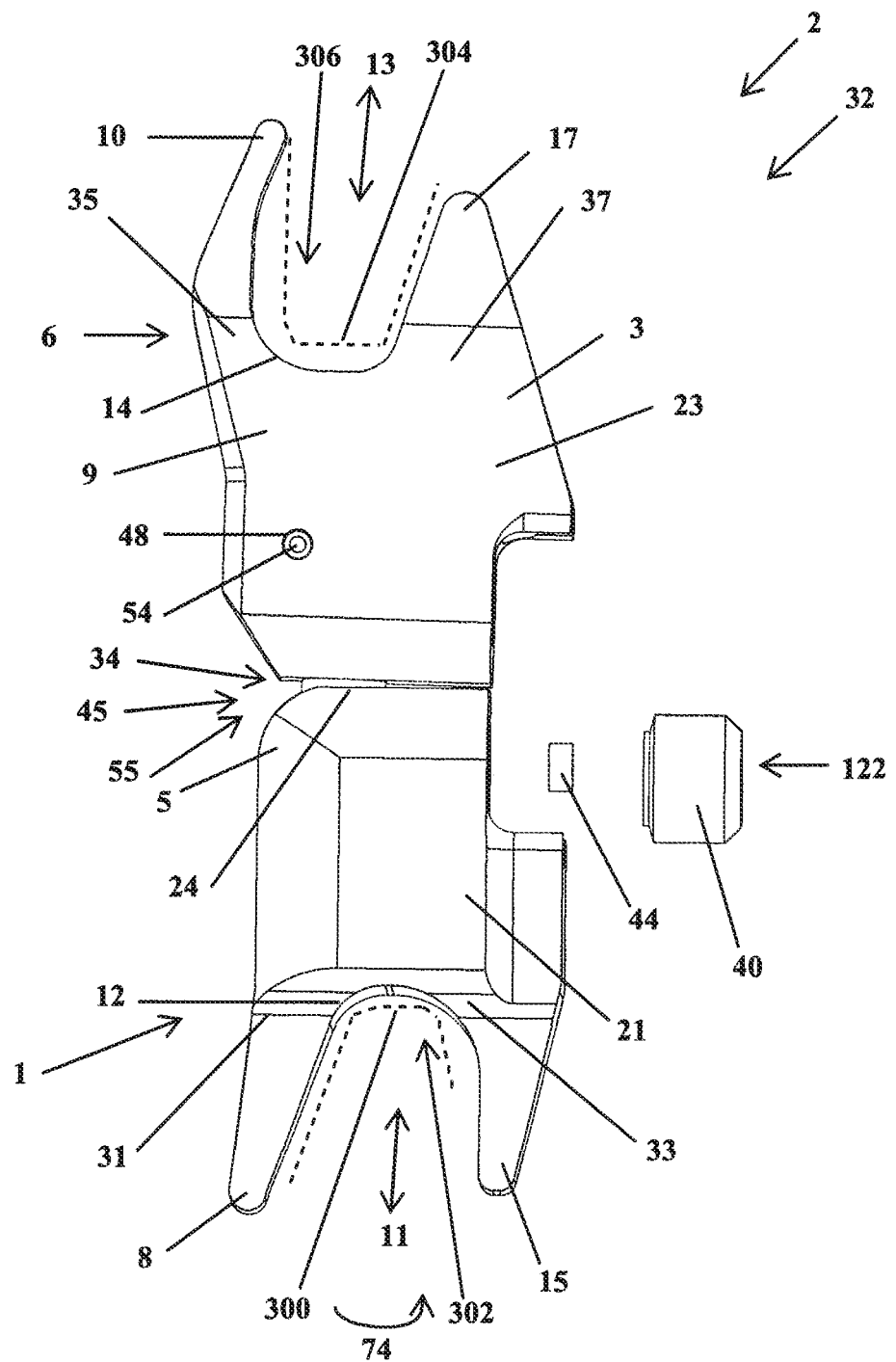
FIG. 4 is a partially exploded side elevational view of the implant device of FIG. 1 showing the superior and inferior hook members in the deployed orientation and an upper hook member set screw and boss member exploded from the upper hook member.

In FIGS. 1-11 and 25-30, a spinal implant device or assembly 2 is shown for being implanted between and variably distracting adjacent vertebral bodies of the human spine, and more specifically the laminae of the adjacent upper and lower vertebrae. The implant device 2 includes an upper or superior hook portion or device 1 for engaging a lower surface 300 of a superior lamina 302, a lower or inferior hook portion or device 3 for engaging an upper surface 304 of an inferior lamina 306, and an elongate guide portion or device 7 connected to each of the upper hook device 1 and the lower hook device 3, as shown in FIGS. 2, 4 and 6. The superior and inferior hook devices 4 and 6 are adjustable relative to the elongate guide device 7 and to each other so that the implant device 2 can be securely engaged between the adjacent upper and lower lamina 302 and 306 substantially irrespective of their geometries relative to each other.

As shown in FIGS. 1-4 and 25-29, the upper and lower hook devices 1 and 3 are preferably hook members 4 and 6 each having a one-piece body 5 and 9 that includes base portion 21 and 23 and a pair of elongate arm portions or arms 8, 15 and 10, 17 for receiving a lamina therebetween. The bodies 5 and 9 have respective seat portion 12 and 14 extending between the proximal ends 31, 33 and 35, 37 of the arms 8, 15 and 10, 17 at the base portion 21, 23 for being engaged by the laminae 302 and 306 so that the arms 8, 15 and 10, 17 extend along the laminar surfaces 300 and 304. As shown in FIG. 4, the upper and lower hook devices 4 and 6 further include hook device longitudinal axes 11 and 13 along which their respective bodies 5 and 9 extend.

Figure 5:
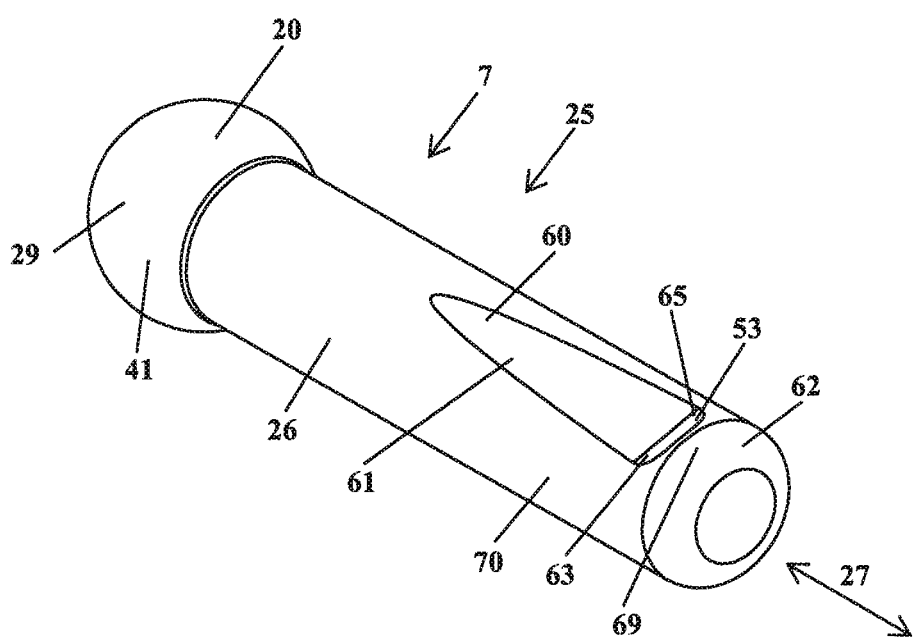
FIG. 5 is a perspective view of the elongate guide member of the implant device of FIG. 1.
Figure 6:
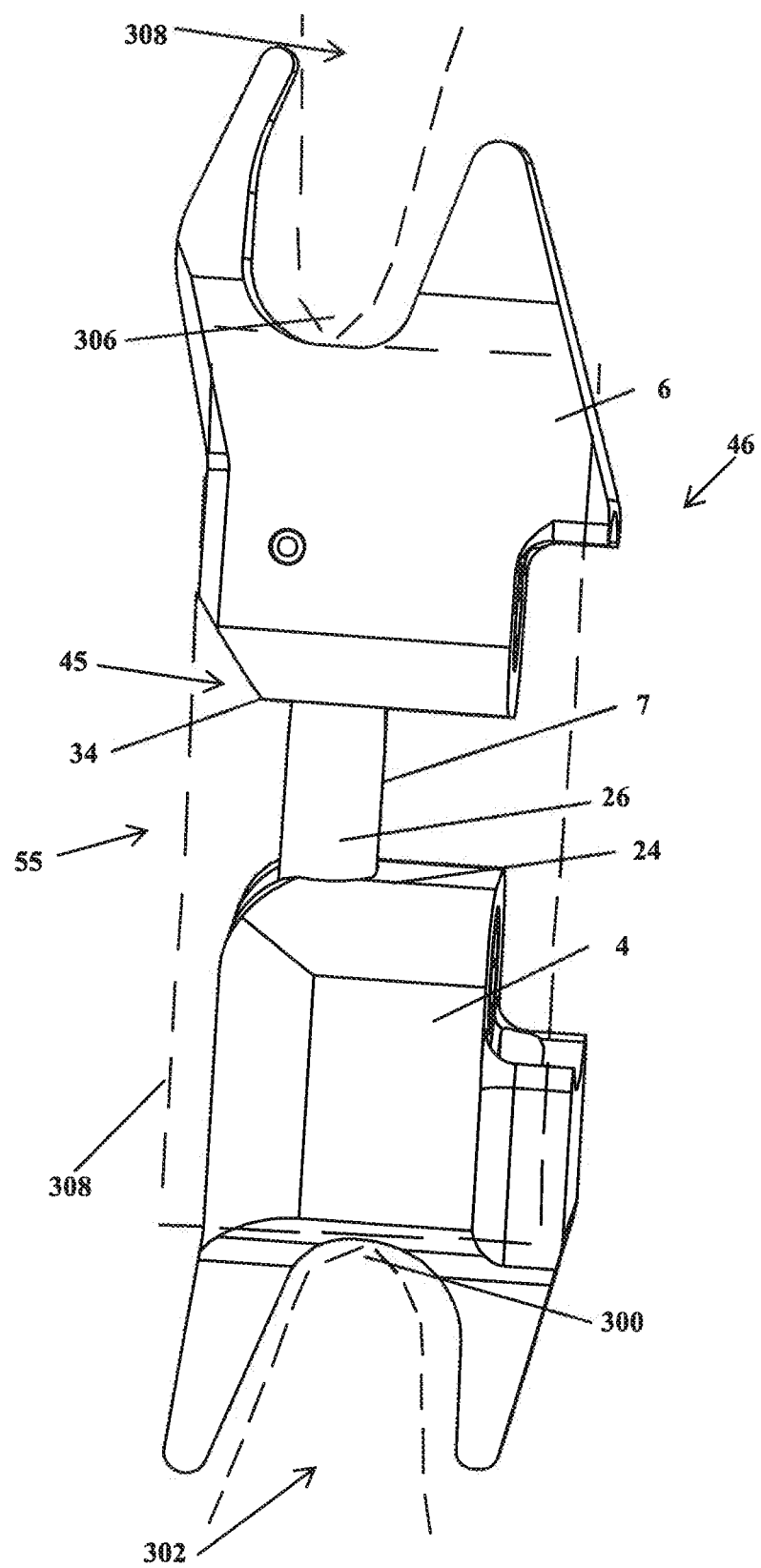
FIG. 6 is a side elevational view of the implant device of FIG. 1 showing the superior and inferior hook members in the distracted orientation.
Figure 10:
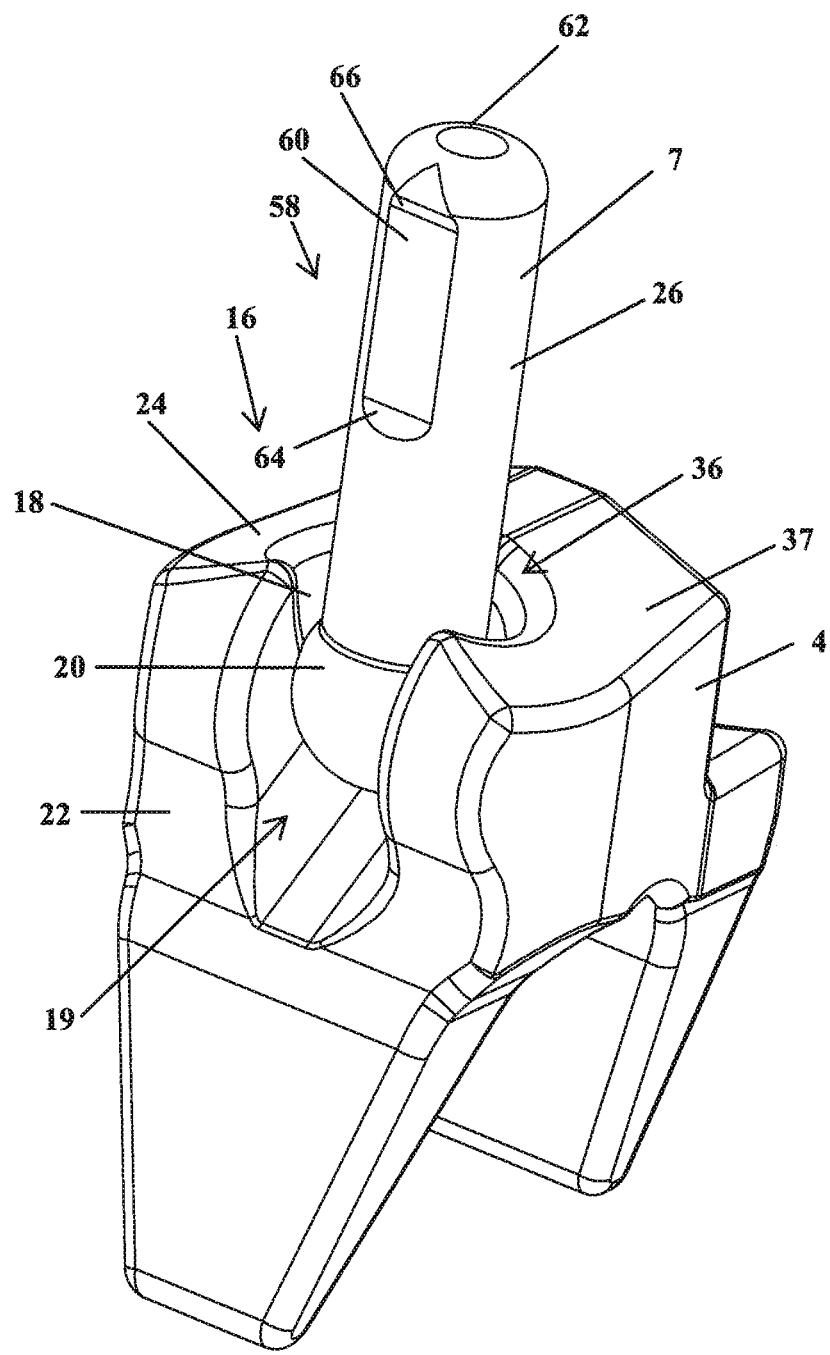
FIG. 10 is a perspective view of the implant device of FIG. 1 showing the superior hook member, alternative elongate guide member and friction rod member of the inferior hook member.

Referring to FIG. 5, the elongate guide device 7 is shown as a being a single piece component in the form of elongate guide member 25 having an elongate shaft 26 extending along longitudinal axis 27 and a radially enlarged portion 20 at one end thereof with the enlarged end portion having a curved bearing surface 29. As shown in FIGS. 1, 2, 10 and 11, one of the hook members 4 and 6, preferably the upper implant hook member 4, is connected to the elongate guide member 7 by a pivot connection 16. As shown in FIG. 10, the pivot connection 16 is preferably a multi-axial pivot connection, such as a ball and socket connection, with the superior hook member 4 including a curved or spherical socket opening 18 extending into the inferior surface 24 of the superior hook member 4 for cooperating with and receiving the radially enlarged end portion 20 in the form of a spherical pivot ball portion 41 of the elongate guide member 7. With the spherical ball portion 20 received in the socket 18, the guide member shaft 26 extends out from the socket opening 18 beyond the inferior surface 24 of the hook member 4.

The pivot connection 16 as described above is a multi-axial pivot connection or universal pivot connection that allows the upper hook member 7 to pivot about multiple axes so as to adjust to the contour of the lamina 302 and 306 with which it is engaged. In addition, such adjustment takes into account variations in the relative positions between the laminar surfaces 300 and 304 engaged by the upper and lower hook members 4 and 6 such as can occur at various locations along and about a particular patient's spine or between different patients.

A slide connection 45 is provided between at least one of the hook members 4 and 6, preferably the lower implant member 6, and the elongate guide device 7, and in particular the shaft 26 of the elongate guide device 7, to allow for distraction of the engaged vertebral bodies to various distances spaced from each other. Preferably, the slide connection 45 includes a detachable or releasable connection 55 which allows the lower hook member 6 to be easily connected to and removed from the shaft 26 of the elongate guide device 7. The detachable connection 55 is preferably a tool-less connection in that the inferior hook member 6 can be removed or disconnected from the elongate guide member 7 and connected to elongate guide member 7 without using a tool. In one form, the releasable connection 55 is a snap-fit connection.

The upper hook member 4 can include a slot 19 extending from the socket 18 along one side 22 of the superior hook member 4. The slot 19 is sized for the shaft 26 to pass therethrough and is configured to provide an increased range of motion of the pivot connection 16. In one embodiment, the slot 19 is configured to allow the superior hook member 4 to be pivoted about the spherical ball portion 20 at least about 90 degrees from the elongate guide axis 27. In an alternative embodiment, the slot 19 is configured to provide pivoting range of at least about 120 degrees, preferably about 135 degrees from the elongate guide axis 27.

Figure 1:
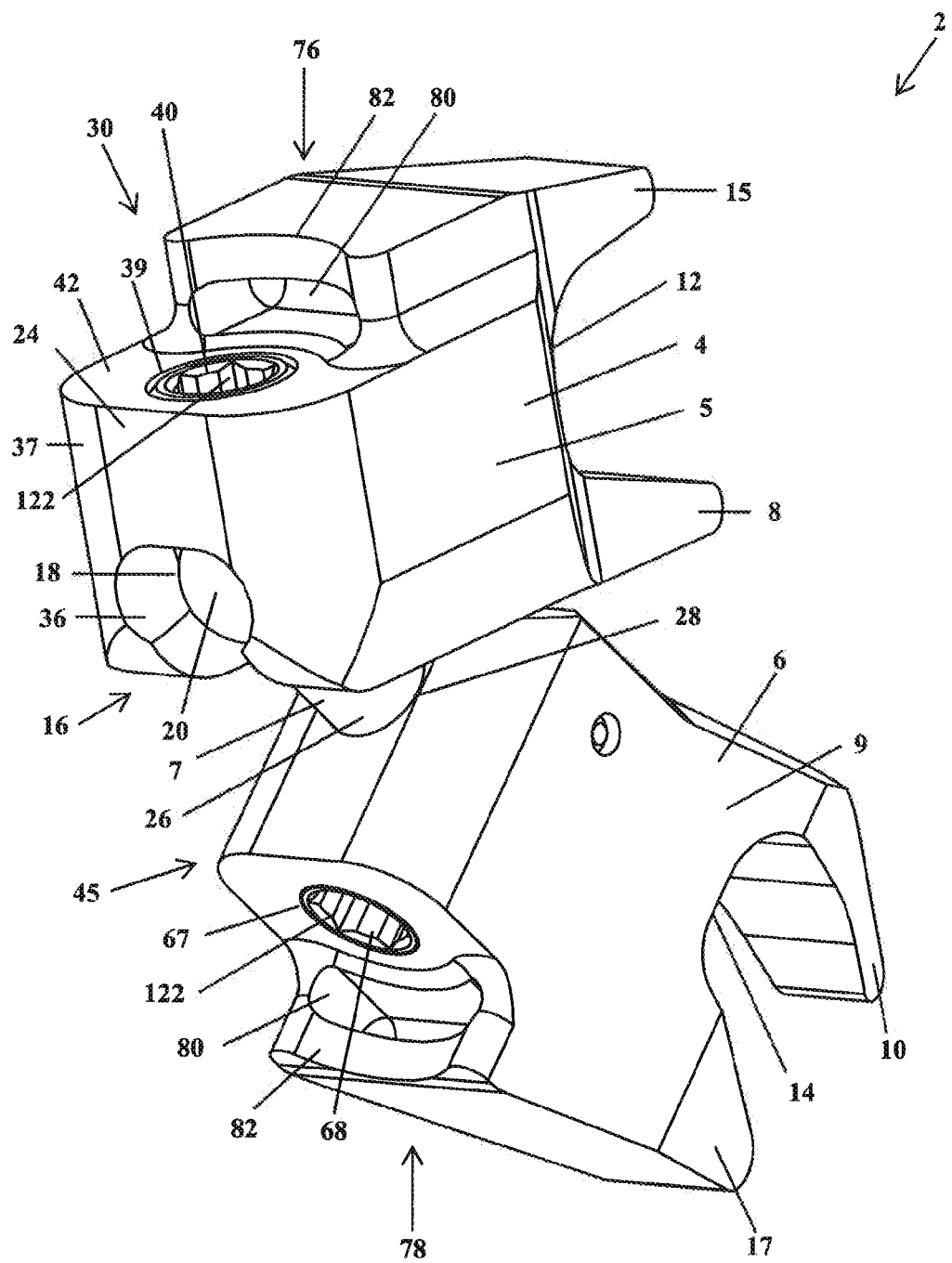
FIG. 1 is a perspective view of the implant device of the present invention showing the superior and inferior hook members in the deployed orientation.

The shaft 26 is further sized to extend through both the socket 18 and the slot 19 and be received in a shaft receiving bore 28 of the lower or inferior hook member 6, as shown in FIGS. 1 and 10.

Figure 11:
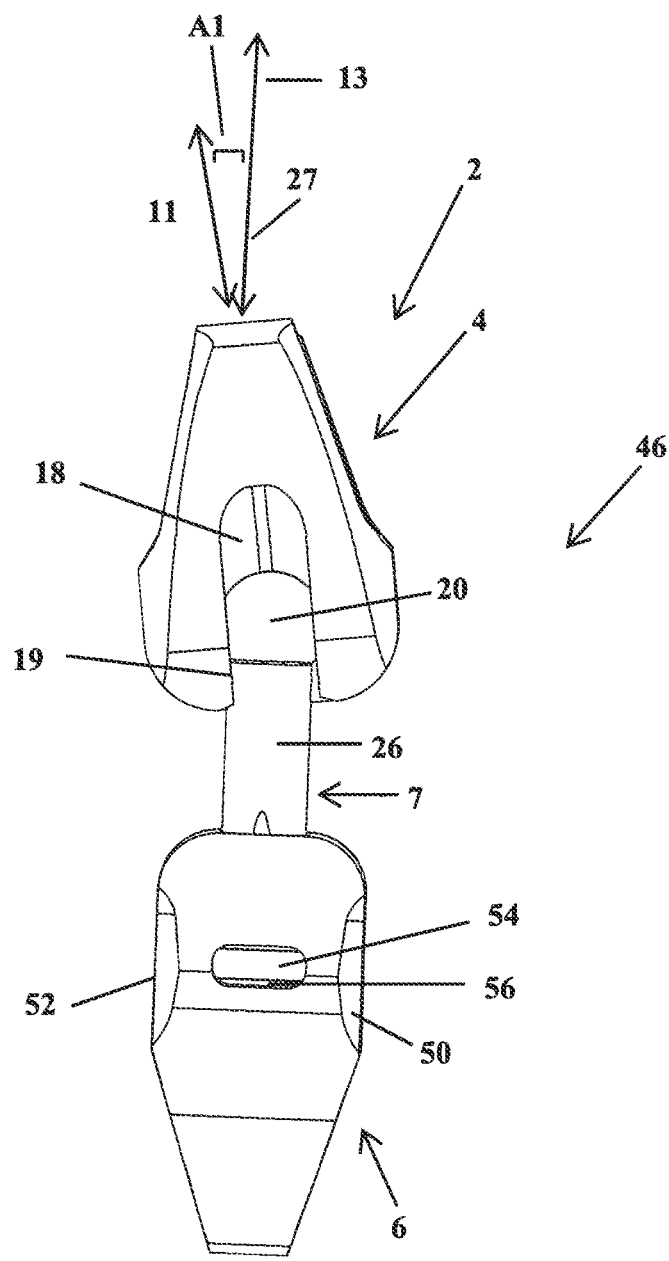
FIG. 11 is an end elevational view of the implant device of FIG. 1 showing the superior and inferior hook members in the extended implantation orientation and the window of the inferior hook member opening to the rod member and the rod receiving bore of the inferior hook member.

As can be seen in FIG. 10, an oversized or enlarged opening 36 in the inferior surface 24 of the superior hook 4 leads to the spherical socket opening 18. The oversized opening 36 is configured to allow the superior hook member 4 to be universally pivoted on the spherical ball portion 20 about multiple axes relative to the elongate guide axis 27 while maintaining the upper and lower hook members 4 and 6 in the compact implanted configuration 32. In particular, the oversized opening 36 is chamfered to minimize interference between the inferior surface 24 of the superior hook 4 and the elongate guide shaft 26 of the elongate guide member 7. In particular, such as shown in FIG. 11, the oversized opening 36 is configured to permit the superior hook 4 to pivot about the spherical guide ball 20 along multiple axes at an angle A1, such as at least about 25 degrees from the elongate guide axis 27 and the lower hook member axis 13. In one embodiment the oversized opening 36 allows for pivoting of the upper hook member 4 so that the hook member axis 11 can be pivoted relative to the guide longitudinal axis 27 and lower hook member axis 13 up to at least about 25 degrees, more preferably at least up to about 15 degrees.

Figure 30:
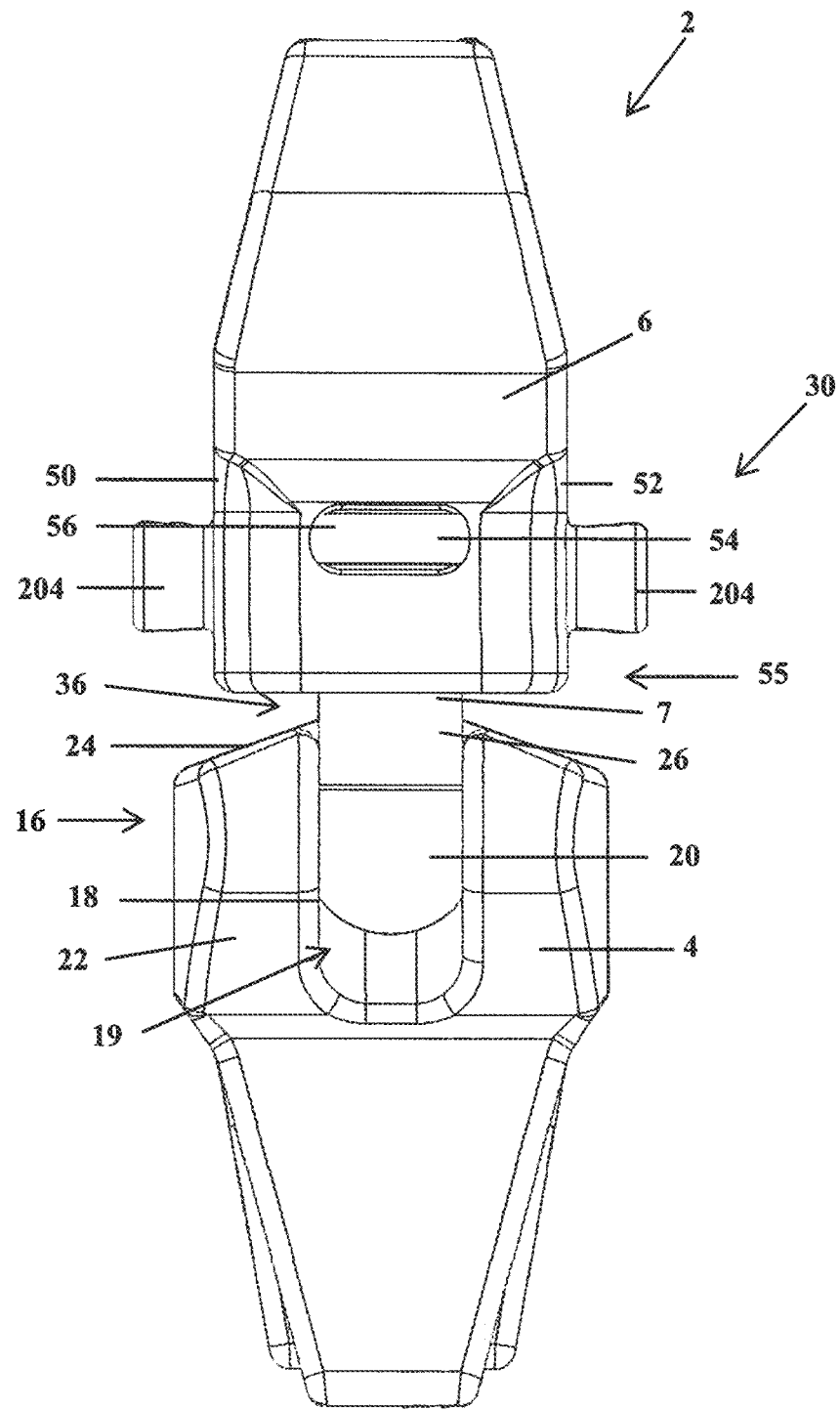
FIG. 30 is an end elevational view of the implant device of FIG. 25 in the compact implanted orientation.
Figure 31:
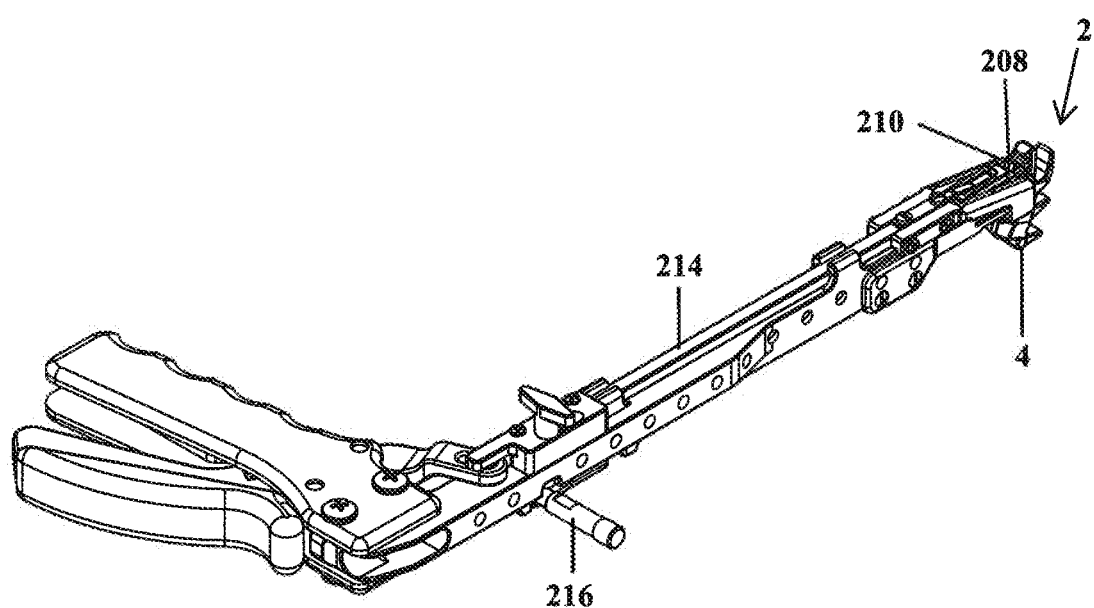
FIG. 31 is a perspective view of an installation tool for implanting the implant of FIG. 25 showing an opening at the grip end for receiving a set screw tightening tool, a pistol grip for adjusting the drive rod, a camming handle for adjusting the location and orientation of the camming tool, and a locking mechanism for securing the drive rod in one of three locations.
Figure 32:
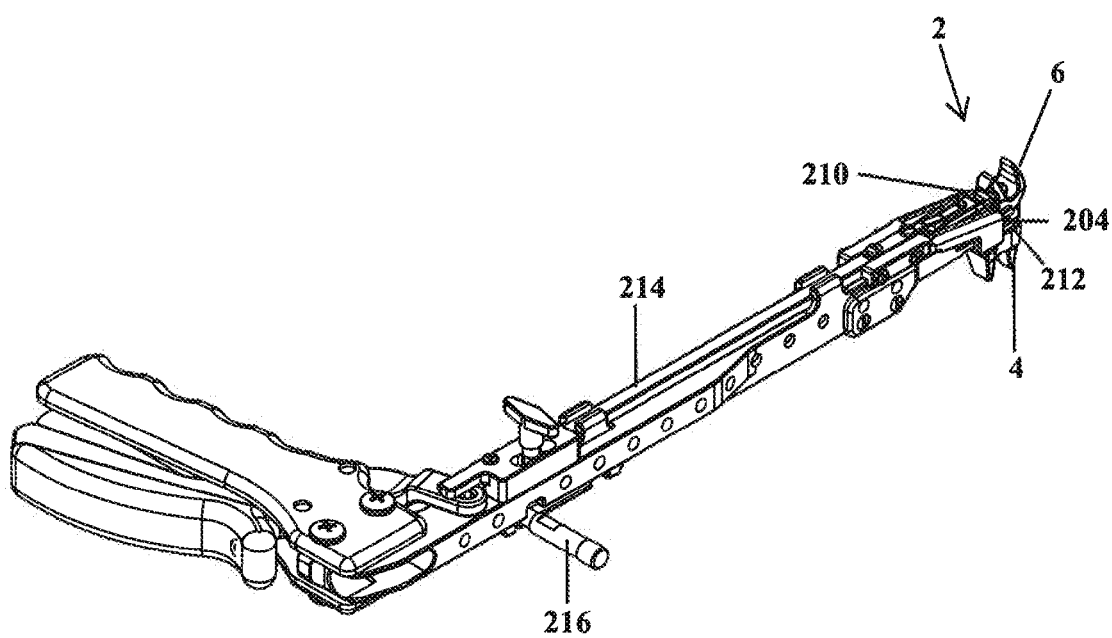
FIG. 32 is a perspective view of the installation tool of FIG. 31 showing the cradles engaging the knobs of the inferior hook member, a pistol grip for shifting a drive rod, the drive rod being connected to a linkage, the linkage connected to the tool engagement boss of the inferior hook member for shifting the hook members from the compact orientation to the deployed orientation.
Figure 33:
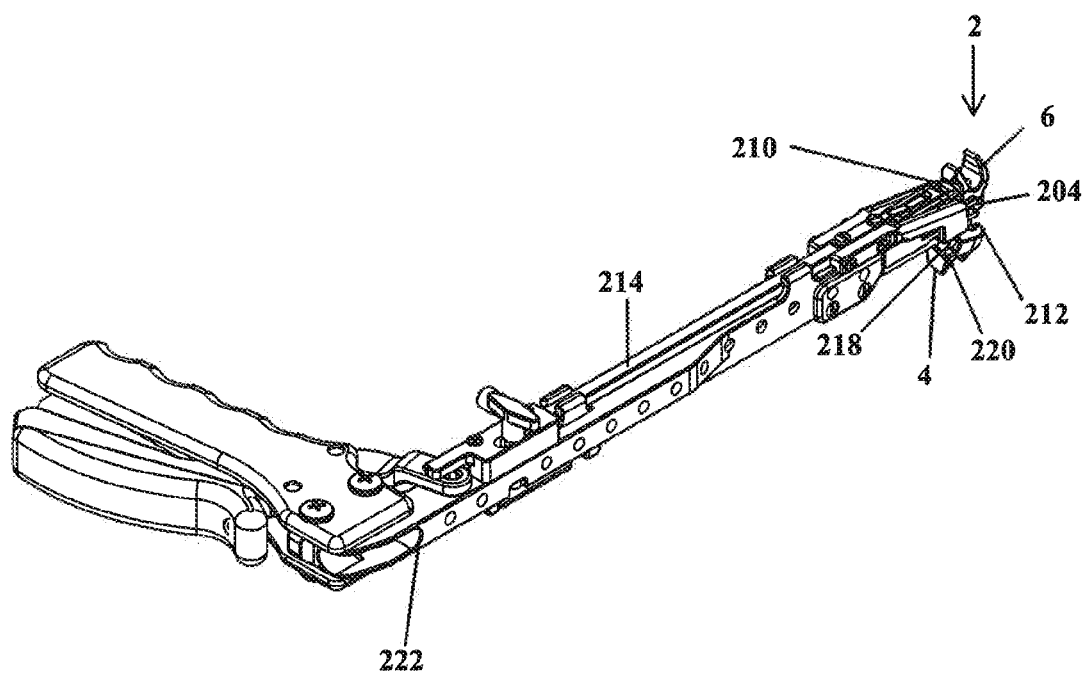
FIG. 33 is a perspective view of the installation tool of FIG. 31 showing the camming handle shifted to a second orientation, a camming portion of the tool engaging a camming surface of the superior hook portion and shifting the superior and inferior hook members from the deployed orientation to the desired distracted orientation.
Figure 34:
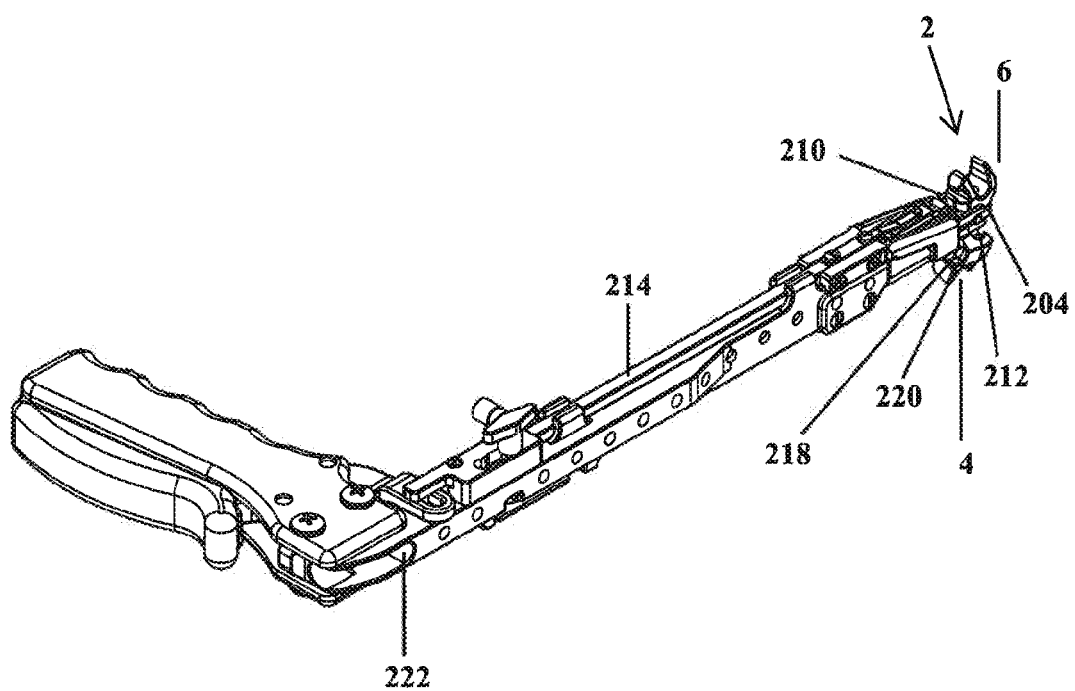
FIG. 34 is a perspective view of the installation tool of FIG. 31 showing the drive rod in the withdrawn orientation, the linkage of the drive rod disengaged from the tool engagement boss of the inferior member, and the installation tool cradle spaced apart to allow the knobs of the inferior hook member to be removed therefrom.

To allow for the pivoting of the superior hook member 4, the inferior surface 24 of the superior hook 4 can be rounded 37, as shown in FIG. 11 or chamfered 38 as shown in FIG. 30 to minimize interference between the superior hook member 4 and the inferior hook member 6 as the superior hook member 4 is pivoted about the elongate guide member 7. More particularly, the rounded surface 37 or chamfered surface 38 can be configured to allow the superior hook member 4 to move freely without the superior surface 34 of the inferior hook 6 abutting the inferior surface 24 of the superior hook 4.

A compact insertion orientation 30 of the hook members 4 and 6 is shown in FIGS. 1 and 2. In the insertion orientation 30, the longitudinal axis 11 of the upper hook member 4 extends transversely and preferably obliquely to the longitudinal axis 27 of the elongate guide device 7 and the longitudinal axis 13 of the lower hook member 6.

The slot 19 is configured such that the pivot connection 16 allows the upper hook member from the compact insertion orientation 30 to a compact implanted orientation 32. As shown in FIGS. 3 and 4, in the compact implanted configuration 32 the inferior surface 24 of the superior hook member 4 faces a superior surface 34 of the inferior hook member 6 such that the seats 8 and 10 of the inferior and superior hook members 4 and 6 extend and face in generally opposite directions. In addition, the axes 11 and 13 of the hook members 4 and 6 and the axis 27 of the elongate guide device 27 are generally aligned, but the upper hook axis 11 can be offset as discussed above due to pivoting of the upper hook member 4 to adjust for the geometries of the engaged lamina 302 and 306, such that the axes 11 and 13 can be offset up to 25 degrees from one another. Further, the longitudinal axis 27 of the guide device 7 extends through the seats 12 and 14 or arms 8 and 10 of each of the hook members 4 and 6 so that the elongate guide device 7 is compactly arranged to extend in the space between the engaged laminae surfaces 300 and 304.

As can be seen in FIGS. 1 and 3, the superior hook member 4 includes a threaded opening 39 extending from an outer surface 42 toward the socket 18 housing the spherical ball portion 20 of the elongate guide member 7. The threaded opening 39 is configured to receive a set screw 40 therein.

In one embodiment, as shown in FIG. 4, the set screw 40 includes a boss portion 44 connected to a distal end of the set screw 40. Preferably, the boss portion 44 comprises a biocompatible material, such as PEEK. The boss portion 44 is configured to engage the spherical ball portion 20 and resist movement of the superior hook member 4 relative to the spherical ball portion 20 by providing frictional resistance. In particular, the set screw 40 can be tightened prior to implantation so that the boss portion 44 engages the spherical ball portion 20 such that the superior hook member 4 can be pivoted relative to the elongate guide member 7 upon the application of sufficient force, but will retain the desired position of the superior hook member 4 relative to the elongate guide member 7 in the absence of any external forces being applied. As a result, when the superior hook member 4 is adjusted to the desired orientation, the boss member 44 provides sufficient frictional resistance to resist any further movement of the superior hook member 4 relative to the elongate guide member 7 absent additional external forces. Once in the desired configuration or orientation, the set screw 40 can be tightened further to increase the resistance applied by the boss member 44 against the spherical ball portion 20 to firmly secure the superior hook member 4 in the desired orientation.

Referring again to the slide connection 45, the lower hook member 6 can be slid or translated from the compact implanted configuration 32 to an extended or distracted implanted configuration 46. In the distracted configuration 46, as shown in FIG. 6, the lower hook member 6 is linearly shifted or translated away from the superior hook member 4 along the elongate axis 27 of the guide shaft 26 of the elongate guide member 7 to provide a desired spacing of the vertebral bodies of each of the engaged laminae 302 and 306. While the distance the inferior hook member 6 is shifted in relation to the superior hook member 4 is determined by the individual geometries of the engaged vertebral bodies, there is no preset number of distraction configurations available for the upper and lower hook members 4 and 6. Generally, the amount of the distraction available is limited by the length of the guide shaft 26. For example, the guide shaft 26 can be sized to provide a distraction distance of up to approximately 4 mm.

As can be seen in FIG. 11, the inferior hook member 6 includes a linearly extending bore 48 extending between side walls 50 and 52 for receiving a rod or pin 54 therein. The bore 48 extends through a window or opening 56 in the inferior hook member 6 located generally central along the width of the hook member 6. Further, the bore 48 extends through a portion of the rod receiving bore 28 of the inferior hook member 6. To ease in insertion, the rod 54 may include chamfered end portions to help guide the rod 54 into the bore 48. In one embodiment, the bore 48 includes a smaller diameter securing portion adjacent one of the sidewalls 50 and 52 sized to snugly receive the rod 54 therein and resist movement of the rod 54 out of the bore 48.

Figure 7:
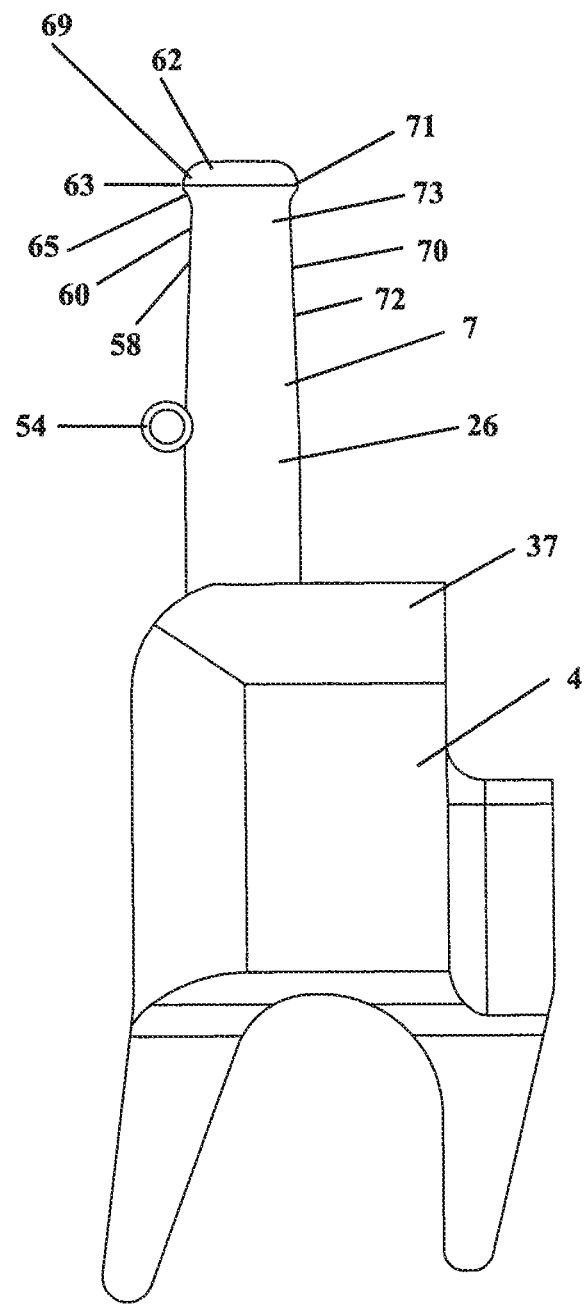
FIG. 7 is a side elevational view of the implant device of FIG. 1 showing the superior hook member, elongate guide member and friction rod member of the inferior hook member.

As indicated in FIG. 7, the bore 48 is positioned so that the rod or pin member 54 can engage a side 58 of the guide shaft 26. In some embodiments, the rod 54 provides frictional resistance on the guide shaft 26 and thereby resists movement of the guide shaft 26 relative to the inferior hook member 6. In particular, the rod member 54 is intended to maintain the location of the guide shaft 26 in relation to the inferior hook member 6 absent the application of external forces thereto.

As can be seen in FIGS. 5 and 7, the guide shaft 26 includes a flattened portion 60 extending from the distal end 62 of the guide shaft 26 to a generally intermediate axial position along the length of the guide shaft 26. As shown in FIG. 7, the rod or pin member 54, such as a nitinol rod, is engaged with the flattened portion 60 of the guide shaft 26. In one embodiment, the flattened portion 60 includes a tapered surface 61 that tapers radially inwardly as it extends toward the distal end 62 of the shaft 26. A radially enlarged portion in the form of a lip 63 is formed at a distal end 65 of the flattened portion 60 which acts as a detent to limit the sliding of the inferior hook member 6 along the shaft 26 when the lip 63 abuts the rod member 54. Additionally, as the inferior hook portion 6 is shifted away from the superior hook portion 4 toward the desired distracted distance, the rod member 54 will shift therewith along the tapered surface 61 with the surface 61 tapering away from the rod 54 so that resistance for such sliding movement of the hook members 4 and 6 away from each other via engagement of the rod member 54 with the tapered surface 61 is substantially avoided.

Figure 8:
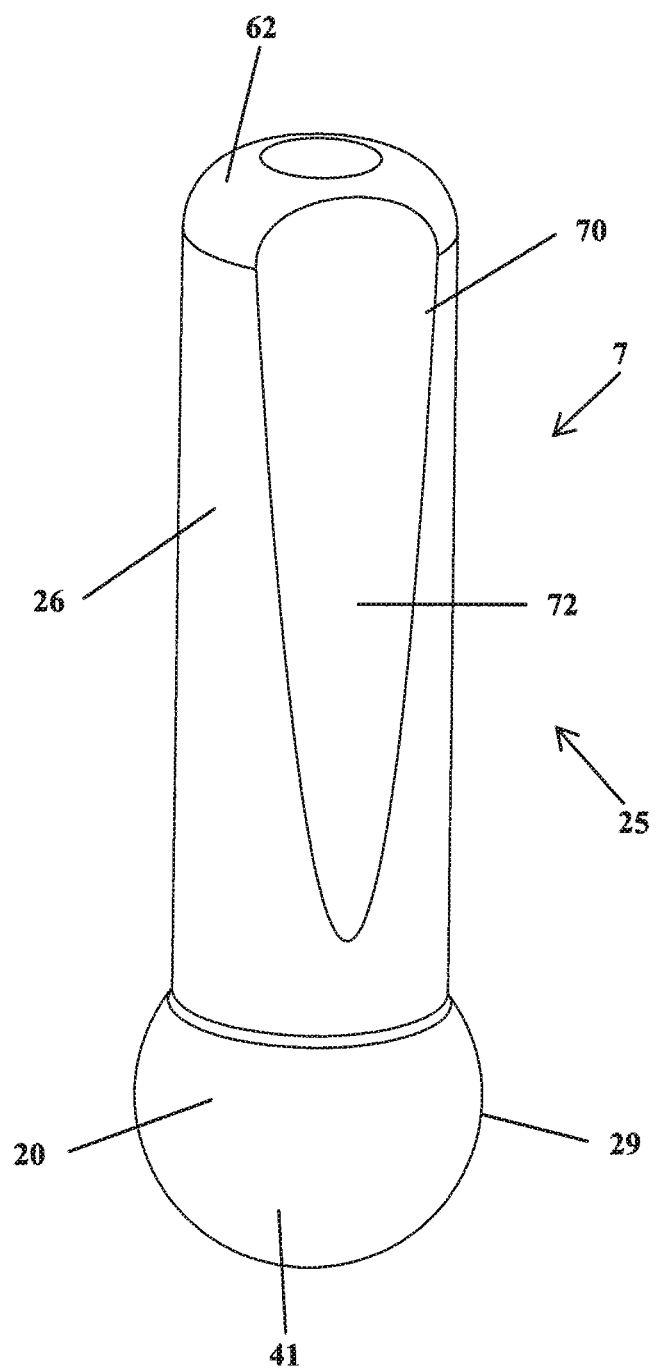
FIG. 8 is a perspective view of an alternative elongate guide member of the implant device of FIG. 1.
Figure 9:
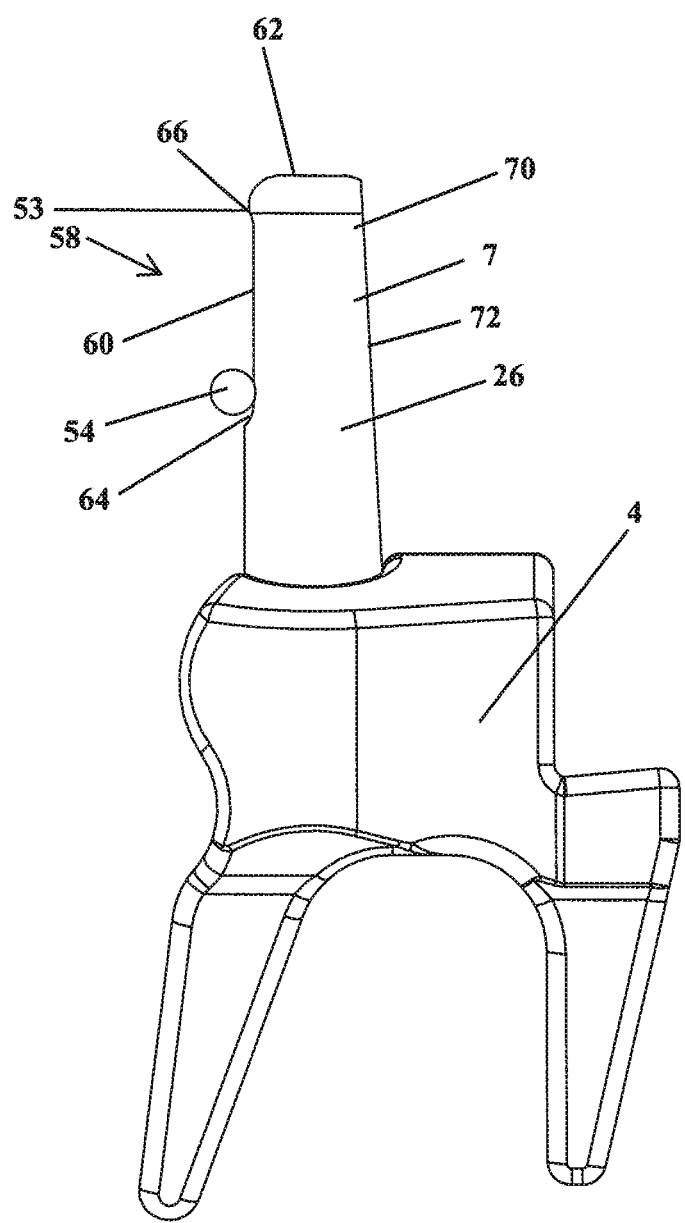
FIG. 9 is a side elevational view of the implant device of FIG. 1 showing the superior hook member, alternative elongate guide member and friction rod member of the inferior hook member.

In an alternative embodiment, as shown in FIGS. 8-10, the flattened portion 60 extends generally parallel to the longitudinal axis 27 of the shaft and is not tapered. At either end of the flattened portion 60 are lips 64 and 66 which act as detents to limit the movement of the inferior hook 6 by abutting the rod member 54 extending through throughbore 48. As the inferior hook portion 6 is shifted toward the superior hook portion 4 and the desired distracted distance, the rod member 54 travels along the flattened portion 60 until the rod member 54 is engaged by the lip or detent 64 adjacent the central portion of the guide shaft 26, thereby stopping the shifting of the inferior hook member 6 toward the superior hook member 4.

The lips or detents 63 or 66 are configured so that the lower hook member 6 can be connected to and disconnected from the elongate guide member 7. In one embodiment, the slide connection 45 of the implant device 2 includes the lips 63 or 66 and the rod 54 which also provide the detachable or releasable connection 55 between the inferior hook member 6 and the elongate guide member 7. As the inferior hook member 6 is shifted or pulled away from the superior hook member 4 the rod member 54 travels along the flattened portion 60 until the rod member 54 engages the radially enlarged lip or detent 63 or 66 adjacent the distal end 62 of guide shaft 26. The distal end lip or detent 63 or 66 acts to limit the travel of the inferior hook member 6 away from the superior hook member 4. However, upon application of sufficient force, the rod member 54 will cam against a camming surface 53 of the lip 63 or 66 to cause the rod 54 to resiliently bow or deform away from the shaft 26 by a sufficient amount so that the lip 63 or 66 adjacent the distal end 62 of the guide shaft 26 can clear the rod 54, thereby disconnecting the inferior hook member 6 from the guide shaft 26 of the elongate support 7. Once the lip 63 or 66 passes the rod 54, the rod 54 will resiliently return or snap back to its undeformed configuration. The window portion 56 of the inferior hook member 6 is sized to provide space for the rod member 54 to bow or deform outwardly sufficiently so that the lip 63 or 66 of the guide shaft 26 can be pulled past the rod member 54 to thereby allow the lower hook member 4 to be pulled off of the guide device 7.

As such, the inferior hook member 6 can be swapped out for an alternatively configured inferior hook member 6 which will more closely match the geometry of the laminar surface 304 to be engaged thereby or to better fit into the space between the upper and lower laminae 302 and 306 to be distracted. The inferior hook member 6 can be reconnected to the elongate guide 7 by positioning the shaft 27 off the elongate guide device 7 within the bore 28 and pushing the inferior hook member 6 toward the upper hook member 4. Upon the application of sufficient force, the rod member 54 will cam against a rounded outer surface 69 of the lip 63 or 66 to cause the rod 54 to resiliently bow or deform away from the shaft 26 by a sufficient amount so that the lip 63 or 66 adjacent the distal end 62 of the guide shaft 26 can clear the rod 54, thereby connecting the inferior hook member 6 to the guide shaft 26 of the elongate support 7. Once the lip 63 or 66 passes the rod 54, the rod 54 will resiliently return or snap back to its undeformed configuration. The window portion 56 of the inferior hook member 6 is sized to provide space for the rod member 54 to bow or deform outwardly sufficiently so that the lip 63 or 66 of the guide shaft 26 can be pushed past the rod member 54 to thereby allow the lower hook member 4 to be connected to the guide device 7. As a result, the modular nature of the upper and lower hook members 4 and 6 allows the surgeon to select or mix and match between a plurality of inferior hook members 6 with the superior hook member 4 to provide the best fit and engagement of the lamina 302 and 306 based on the individual geometry at the implantation location.

As shown in FIGS. 1 and 3, the inferior hook member 6 can include a threaded throughbore 67 positioned opposite the window 56 of the inferior hook member 6 and extending into the receiving bore 28 of the inferior hook member. The threaded throughbore 67 is configured to receive a set screw 68 therein to engage and secure the guide shaft 26 in the desired location within the receiving bore 28 of the inferior hook member 6. When engaged with the guide shaft 26, the set screw 68 can resist compressive forces applied to the upper and lower hook members 4 and 6 during use while maintaining the desired distracted distance.

As shown in FIGS. 5, 7, 8 and 9, adjacent the set screw 68 the guide shaft 26 can include a flattened section 70 for being engaged by the set screw 68. In particular, the depth of flattened portion 70 along the guide shaft 26 tapers toward the distal end 62 so as to reduce the profile of the guide shaft 26 along its length toward the distal end 62. This tapered configuration acts to further resist the compressive forces applied during implantation and use of the implant device 2. In particular, the tapered configuration acts as a ramp 72 against which the set screw 68 abuts upon the application of a compressive force to the upper and lower hook members 4 and 6. As a result, the set screw 68 resists the movement of the inferior hook member 6 in relation to the guide shaft 26 not only by the frictional forces resulting from the engagement of the set screw 68 with the guide shaft 26, but also as the result of the guide shaft 26 having an increased profile toward the ball portion 20 which counteracts the compressive forces. As shown in FIG. 7, the guide shaft 26 can further include a radially enlarged lip or detent 71 at the distal end of the flattened portion 73 to limit the translation of the lower hook member 6 along the elongate guide member 7. In one embodiment, as shown in FIGS. 5 and 7, the guide shaft 26 can include identical flattened sections 60 and 70 having identical tapered surfaces 61 and 72 with identical lips 63 and 71. As a result, lower hook member 6 can be installed such that the rod 54 and the set screw 68 engage either of the flattened surfaces 60 and 70.

As shown in FIGS. 4 and 27-29, the configuration of the upper and lower hook members 4 and 6 can act to maintain the orientation of the upper and lower hook members 4 and 6 during use. In particular, as shown in FIG. 4, the seat portion 12 of the superior hook member 4 is offset from the guide shaft 26 and the seat 14 of the inferior hook member 6. The offset positioning of the seat 12 urges the hook members 4 and 6 toward the expanded/distracted orientation 32 and 46 and away from the compact orientation 30. In more detail, the offset application of the force on the superior hook member seat 12 creates a moment 74 about the superior hook member 4 which urges the superior hook member 4 away from the compact orientation 30.

Installation of the implant device 2 includes shifting the upper and lower hook members 4 and 6 relative to the elongate guide member 7. As indicated above, the upper hook member 4 is configured to engage an inferior surface 300 of an upper lamina 302 while the lower hook member 6 is configured to engage an upper surface 304 of a lower lamina 306 adjacent the upper lamina 302. The hook members 4 and 6 are configured such that, in the compact insertion orientation 30, an inner surface 71 of the elongate arm 8 engages a lower surface 300 of the upper lamina 302, and an inner surface 73 of the elongate arm 10 of the inferior hook member 6 engages an upper surface 304 of the lower lamina 306. As can be seen, the inner surfaces 71 and 73 of the arms 8 and 10 are configured to cooperate with the seats 12 and 14 to provide a smooth, uninterrupted transition therebetween so that the inner surfaces 71 and 73 extend down along the arms 8 and 10 and curve into their respective seats 12 and 14 which then similarly smoothly and in an uninterrupted fashion transition to inner surfaces 77 and 79 of the respective arms 15 and 17 which extend up therealong.

Once so positioned, the implant device can be shifted to the compact implantation configuration 32. As discussed above, the seats 12 and 14 of the hook members 4 and 6 engage the upper and lower laminar surfaces 300 and 304 with the implant device 2 in the compact implantation configuration. The upper hook member 4 can be pivoted about the spherical portion 20 of the elongate guide member 7 so that the longitudinal axis 11 of the upper hook member 4 is generally aligned with the elongate guide axis 27. As the upper hook member 4 is pivoted, the upper and lower hook member 4 and 6 are shifted with the guide device 7 into the envelope 308 between the engaged laminar surfaces 300 and 304. The upper and lower hook members 4 and 6 are pivoted relative to the laminae 302 and 306 such that the upper and lower surfaces of the laminae 300 and 304 shift along the inner surfaces 71 and 73 of the arms 8 and 10 toward the seats 12 and 14. Once the upper and lower lamina surfaces 300 and 304 are in engagement with the seats 12 and 14, the implant device 2 will be in its compact implantation orientation 32 in the laminar envelope 308 with the axes 11 and 13 of the hook members 4 and 6 generally extending parallel or coaxial to each other. As described earlier, depending on the relative positions of the laminar surfaces 300 and 304, it is also possible for the axes 11 and 13 to extend at a slight acute angle relative to one another.

Once in the compact implanted the lower hook member 6 can then be translated along the guide shaft 26 of the elongate guide member 7 toward the extended implantation configuration 46 to distract the laminar surfaces 300 and 304 a desired amount. If necessary, the upper hook member 4 can be pivoted to adjust for the geometries of the laminar surfaces 300 and 304. The set screws 40 and 68 can then be tightened to secure the upper and lower hook members 4 and 6 as appropriate in the extended implanted orientation 46.

As shown in FIGS. 1-3, the implant device 2 includes tool engagement portions 76 and 78 of the upper and lower hook members 4 and 6. The tool engagement portions 76 and 78 can include tool engagement recessed pockets 80 adjacent the sets screws 40 and 68 for being engaged by an insertion tool 84. The hook members 4 and 6 can further include curved tool seats 82 adjacent the tool engagement recesses 80.

As shown in FIGS. 12, 20, 23 and 24, implantation of the implant device 2 can include the use of the insertion tool 84 and a hex driver tool 86. The insertion tool 84 includes two member engagement tools 88 and 90 each having a handle assembly 92 having a shaft assembly 94 extending therefrom, with the shaft assembly 94 connected to a hook member engagement assembly 96 and 98. As shown in FIGS. 15-19, the hook member engagement assemblies 96 and 98 includes a set screw tightening assembly 100 configured to engage the hook member set screws 40 and 68 and a tab 102 for being received in the tool engagement recess 80 of the hook members 4 and 6.

Figure 19:
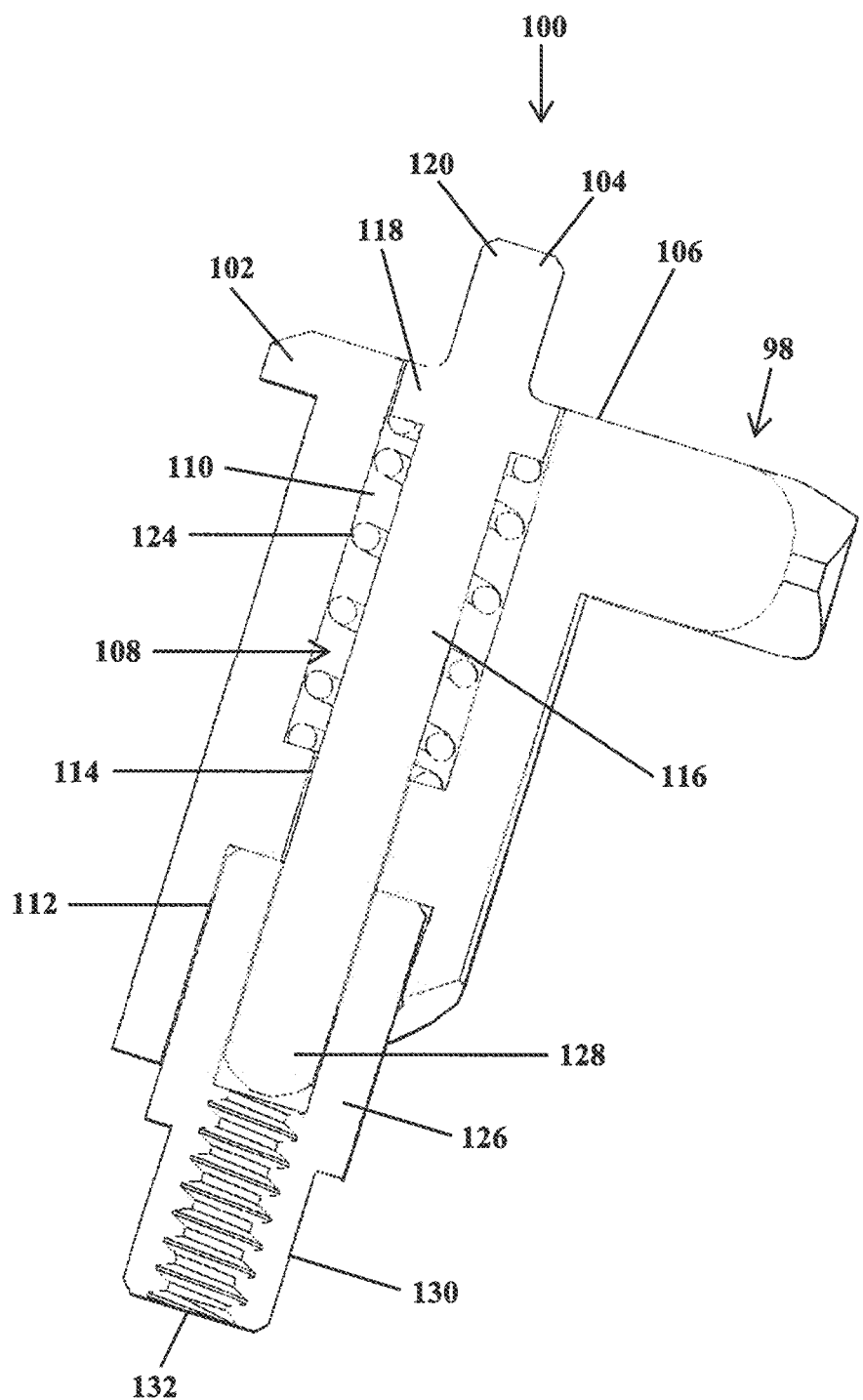
FIG. 19 is a cross section side view of the insertion tool coupler of the insertion tool of FIG. 12.

As shown in FIGS. 12 and 15-17, a screw engagement end 104 of the set screw tightening assembly 100 extends beyond an outer surface 106 of the hook member engagement body 96 and 98. To assist in engagement with the hook member 4 and 6, the hook member engagement body 96 and 98 and the set screw tightening assembly 100 are configured to permit the set screw tightening assembly 100 to be shifted away from the set screw 40 and 68 during installation and removal. As shown in FIG. 19, the hook member engagement body 96 and 98 includes an opening 108 for receiving the set screw tightening assembly 100, including two larger diameter sections 110 and 112 separated by a smaller diameter section 114. A central shaft 116 of the set screw tightening assembly 100 is configured to extend through the larger diameter sections 110 and 112 and smaller diameter section 114. The set screw engagement end 104 of the central shaft 116 includes a larger diameter section 118 corresponding to the larger diameter 110 of the hook member engagement body opening 108 and a male screw engagement end 120 corresponding to a tool engagement portion 122 of the set screw 40 and 68. A spring member 124 is disposed about the central shaft 116 within the larger diameter section 110 between the smaller diameter section 114 and the larger diameter central shaft portion 118. The spring member 124 is configured to bias the central shaft 116 outwardly toward the set screw 40 and 68. A distal tool engagement cap 126 is secured to a distal end 128 of the central shaft 116 and includes an outer tool engagement surface 130 and a threaded bore 132 extending into the distal end 128 of the distal tool engagement cap 126.

After the upper and lower hook members 4 and 6 have been engaged by insertion tools 88 and 90, the implant device 2 is positioned in the compact insertion orientation 30 and positioned so that the upper and lower hook members 4 and 6 engage the appropriate laminar surfaces 300 and 304. Once in place, the handles assemblies 92 of the insertion tools 88 and 90 can be moved to shift the implant device 2 from the insertion orientation 30 to the compact implanted orientation 32 while further inserting the implant device 2 into the interlaminar space. A boss projection 134 of the lower hook member engagement body 98 includes a concave curved surface 136 for engaging a corresponding convex surface 138 of the upper hook member engagement body 96. Prior to securing the set screws 40 and 68 of the hook members 4 and 6, the inferior hook member 6 can be translated along the elongate guide member 7 prior to or after the handle members 92 and shafts 94 of the insertion tools 88 and 90 are repositioned to allow access to the set screws 40 and 68.

Figure 23:
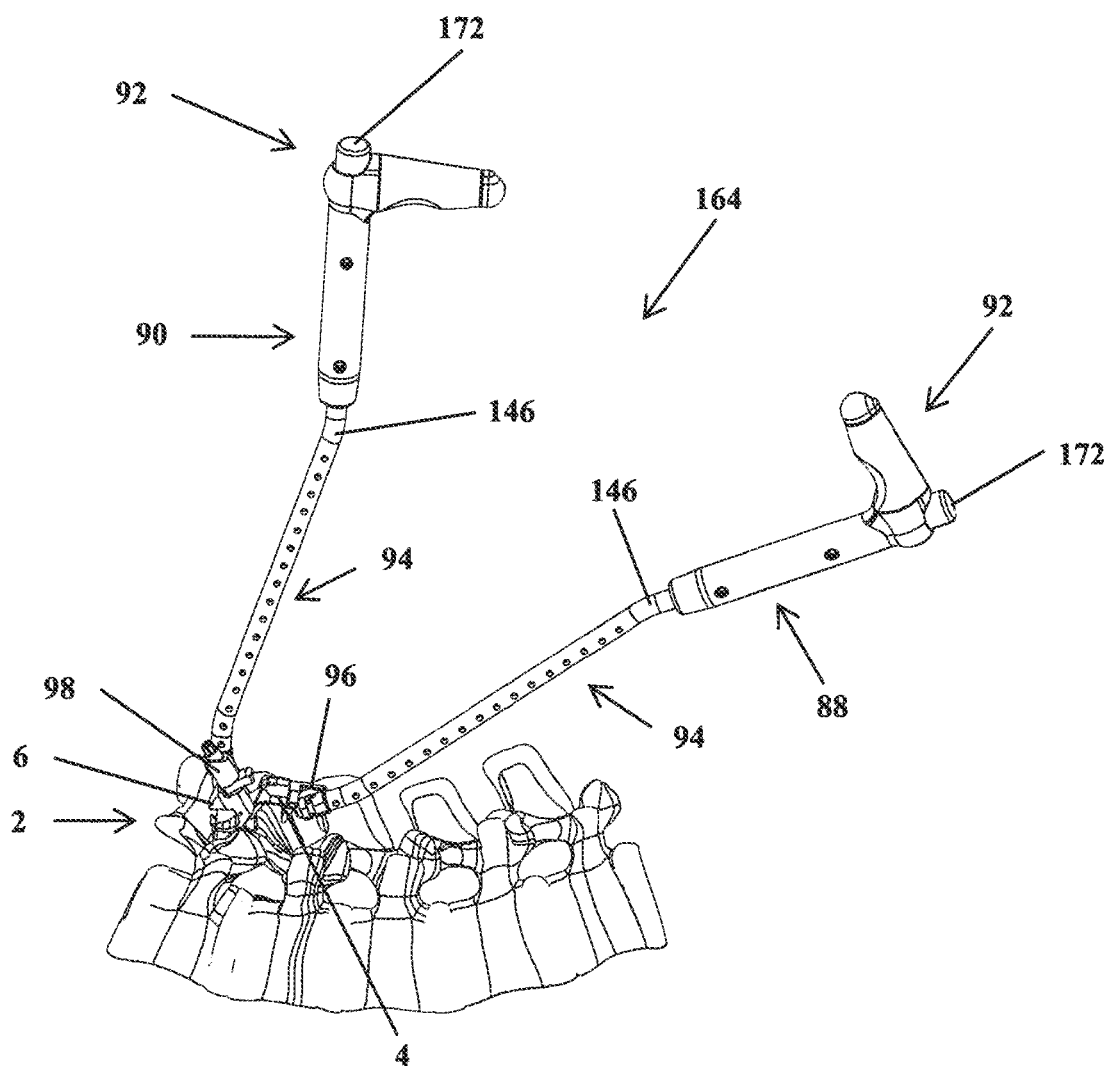
FIG. 23 is a perspective view of the implant device of FIG. 1 in the compact insertion orientation engaged by the insertion tool of FIG. 12.
Figure 24:
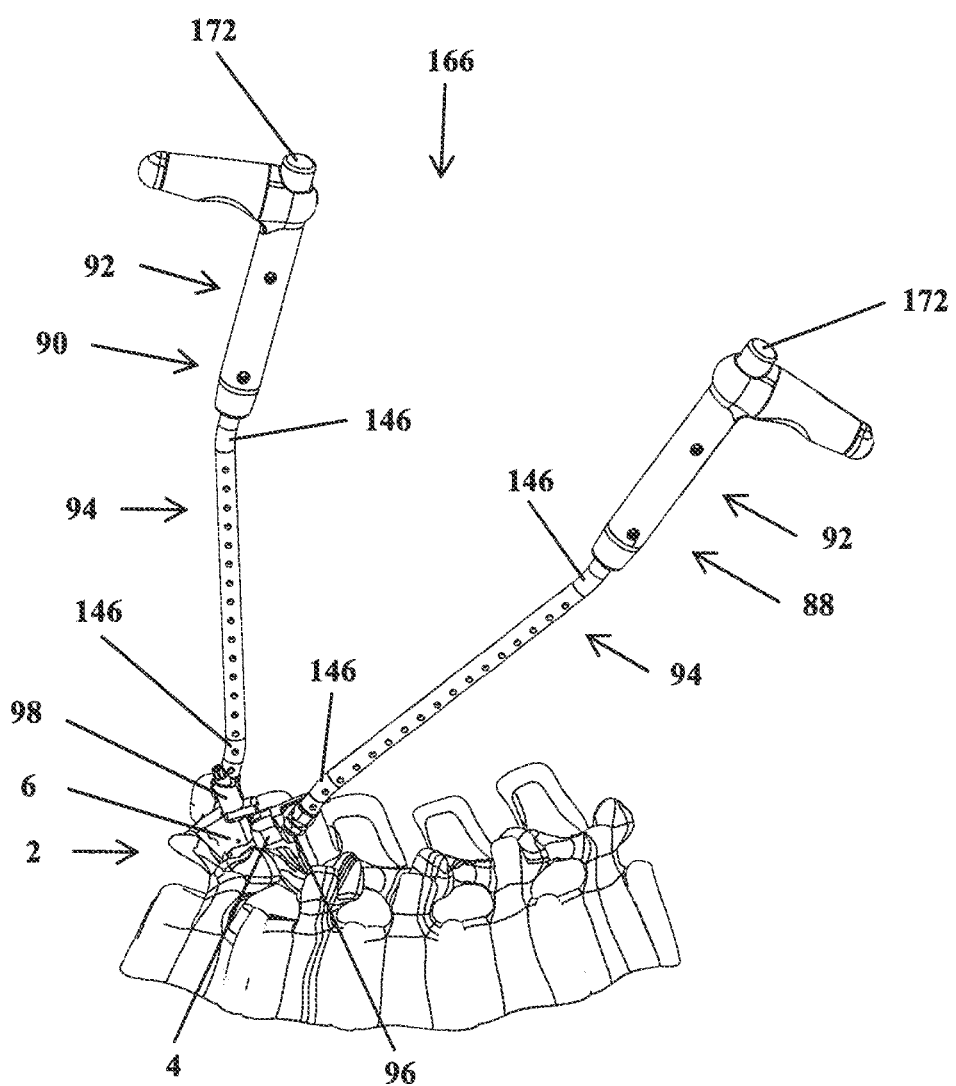
FIG. 24 is a perspective view of the implant device of FIG. 1 in the compact implanted orientation engaged by the insertion tool of FIG. 12.
Figure 25:
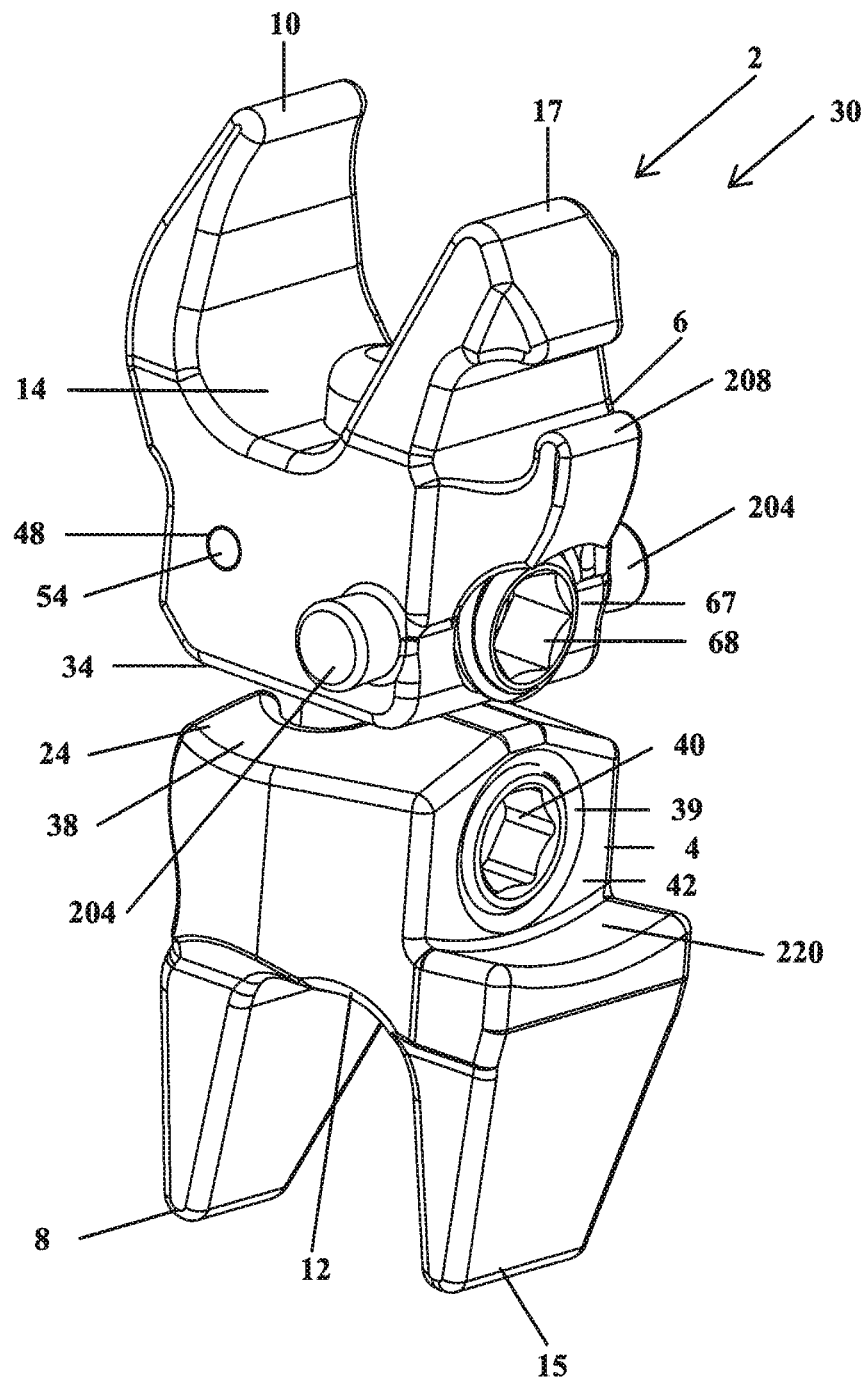
FIG. 25 is a perspective view of an alternative implant device having tool engagement portions extending outwardly from the inferior hook member.
Figure 26:
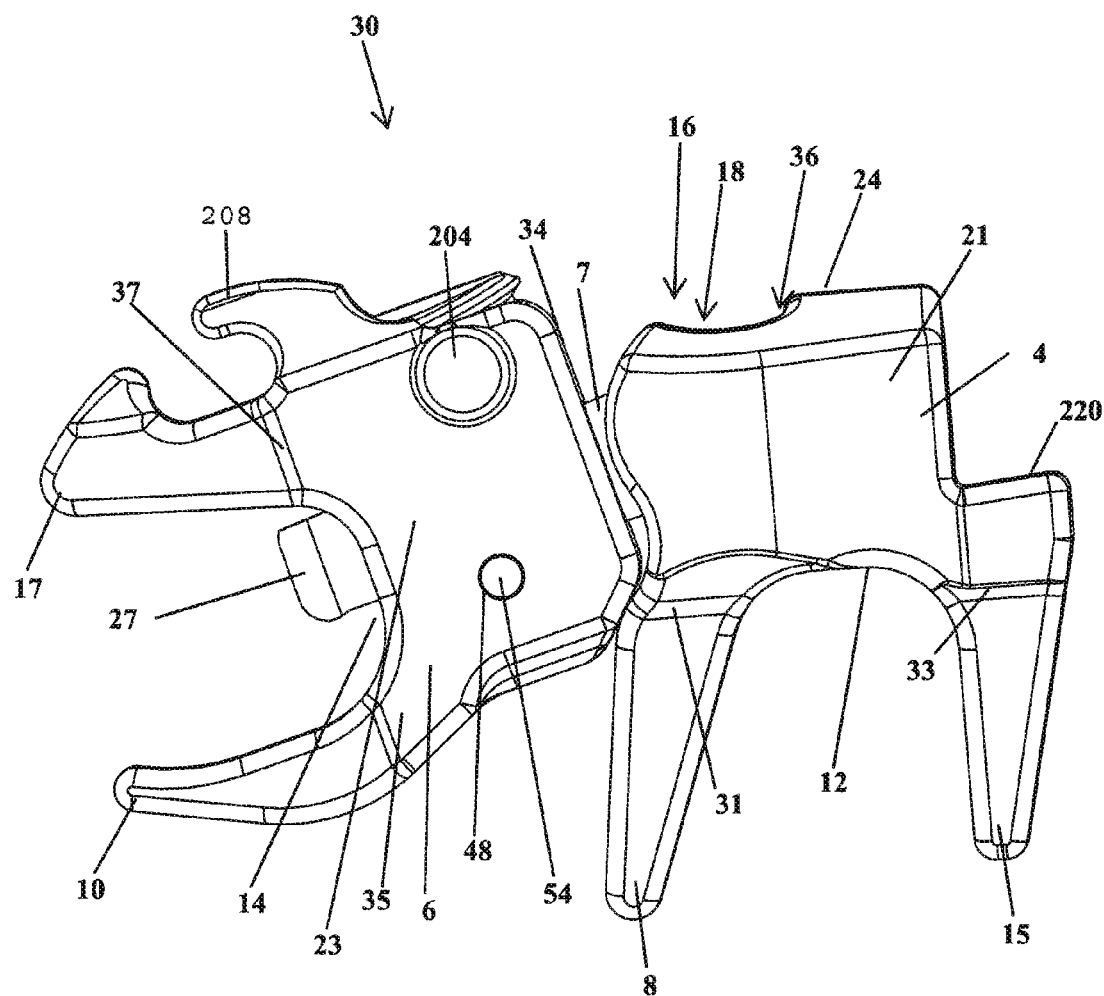
FIG. 26 is a side elevational view of the implant device of FIG. 25 in the compact insertion orientation.
Figure 27:
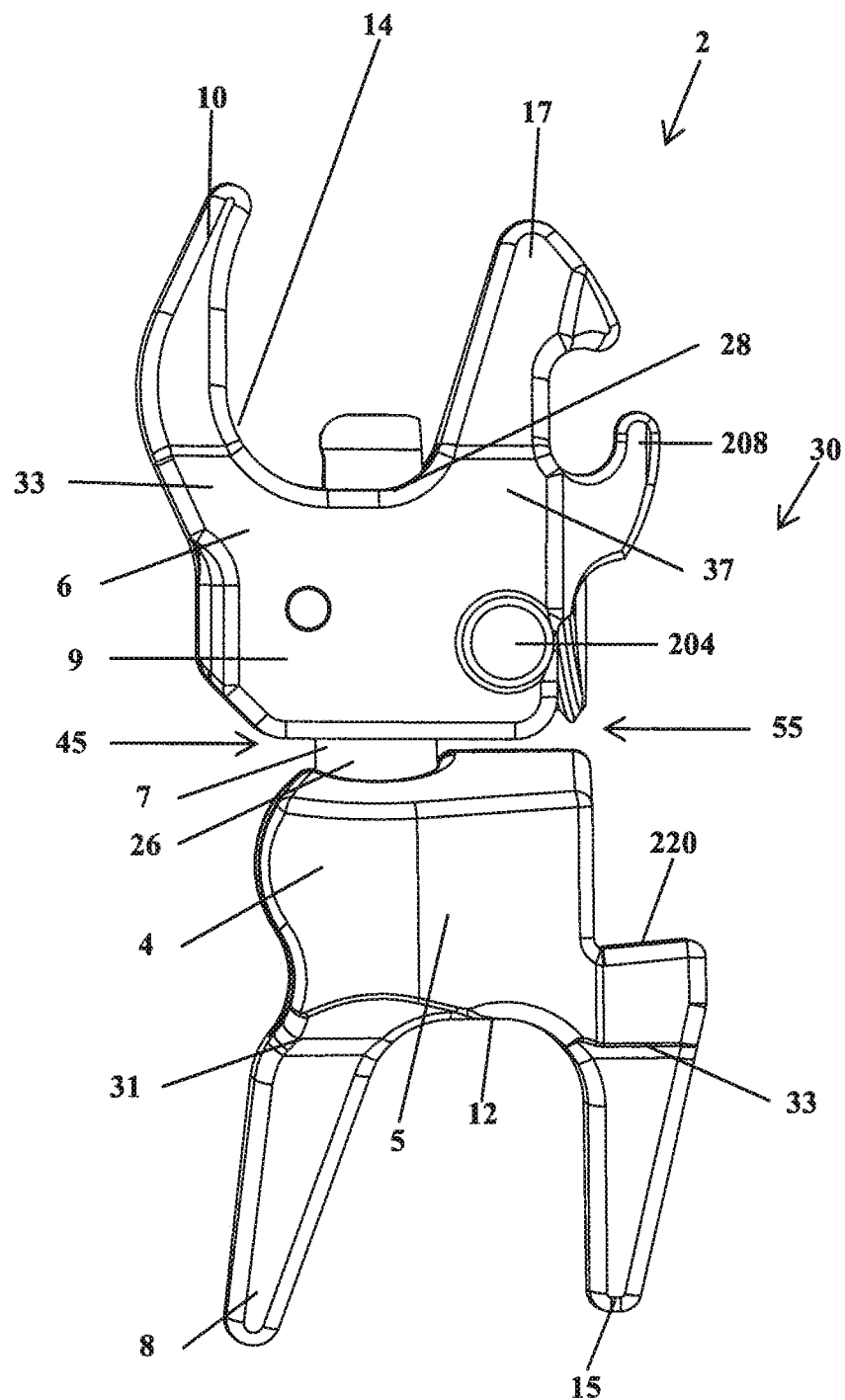
FIG. 27 is a side elevational view of the implant device of FIG. 25 in the compact implanted orientation.
Figure 28:
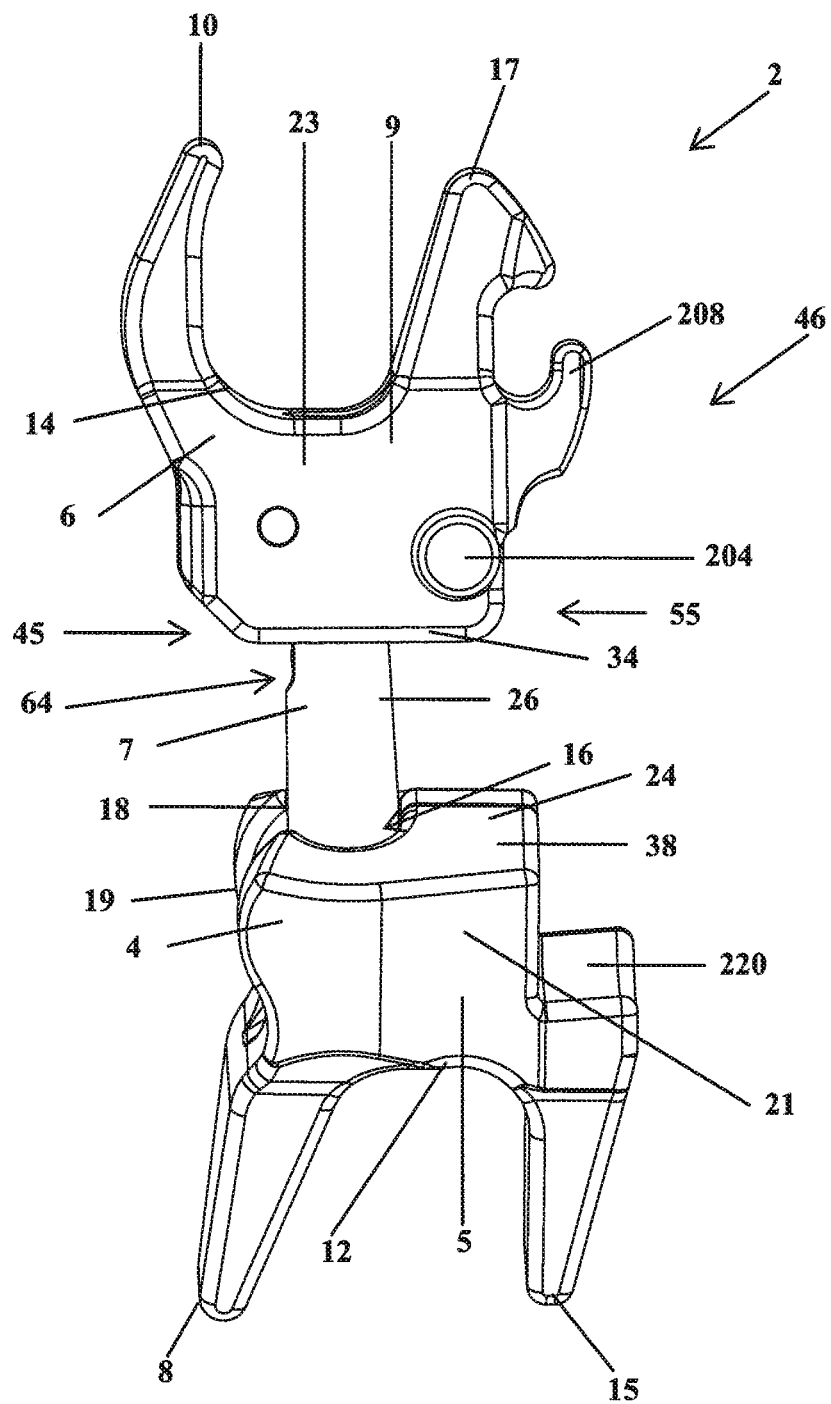
FIG. 28 is a side elevational view of the implant device of FIG. 25 in the distracted orientation.
Figure 29:
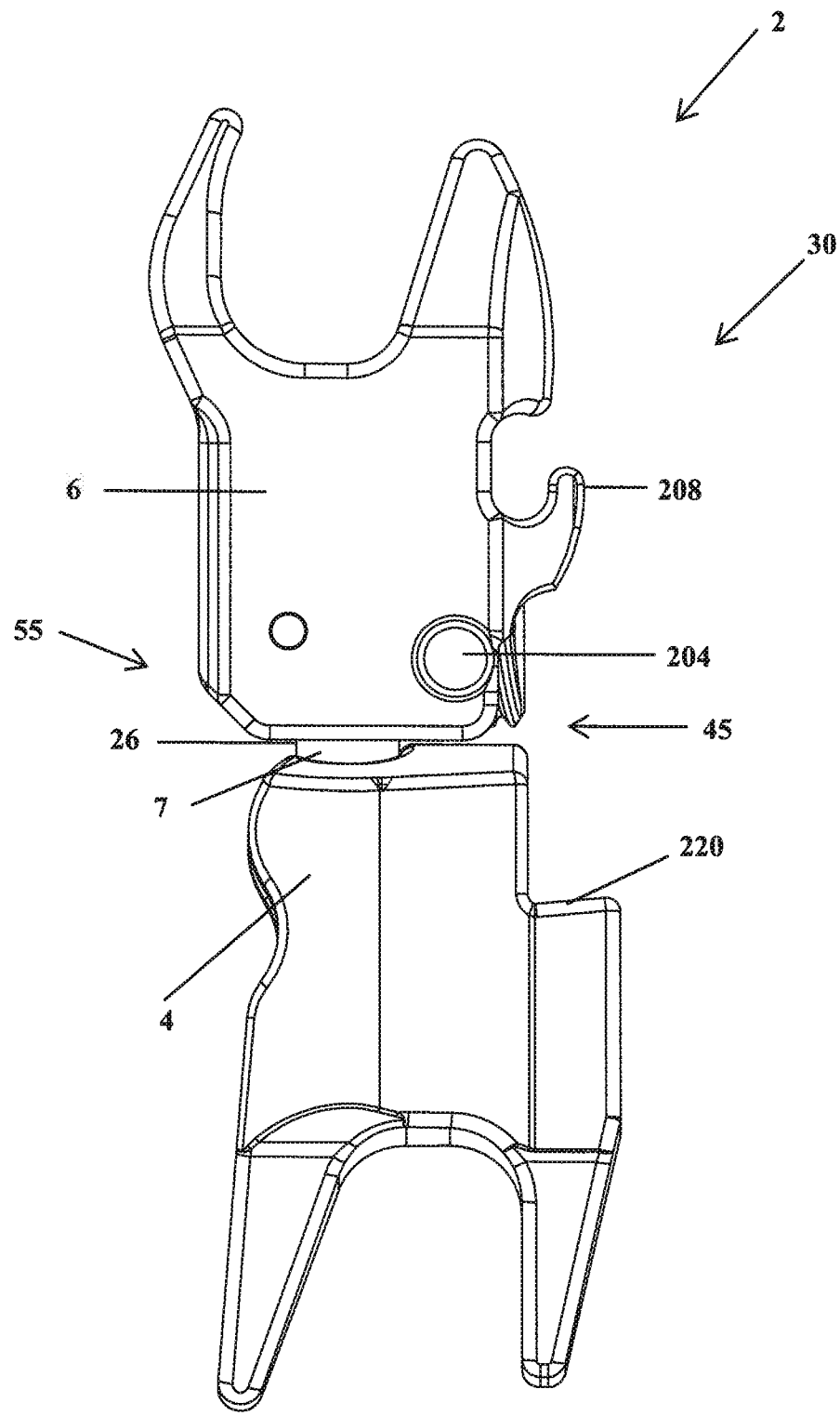
FIG. 29 is a side elevational view of the implant device of FIG. 25 in the compact implanted orientation having enlarged hook members.

As shown in FIGS. 13 and 15-17, the hook member engagement body 96 and 98 includes a pair of outwardly extending spaced flanges 140 and 142. The shaft assembly 94 includes a hollow rigid outer sheath 144 securely fastened to the handle assembly 92. As shown in FIGS. 23 and 24, the hollow rigid outer sheath 144 includes curved sections 146 to aid in inserting the implant device 2 and, after being shifted, to extend outwardly away from the implantation site, to provide a clear line of site to the implant device 2 and engaged laminar portions. The hollow rigid sheath 144 further is configured to engage an outer surface 148 of the primary flange 140 of the hook member engagement body 96 and 98.

Figure 12:
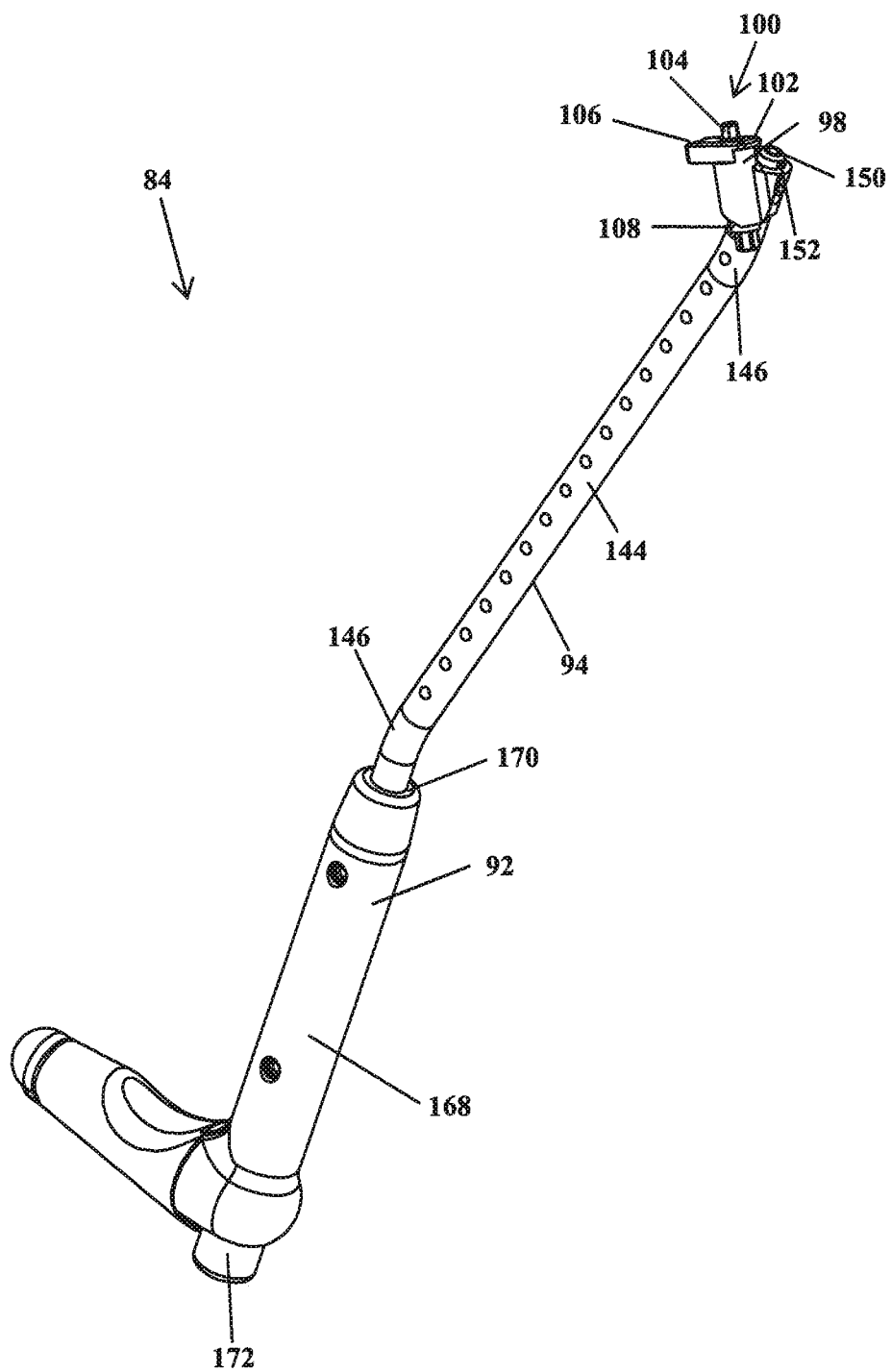
FIG. 12 is a perspective view of an insertion tool for implanting the implant device of FIG. 1.
Figure 13:
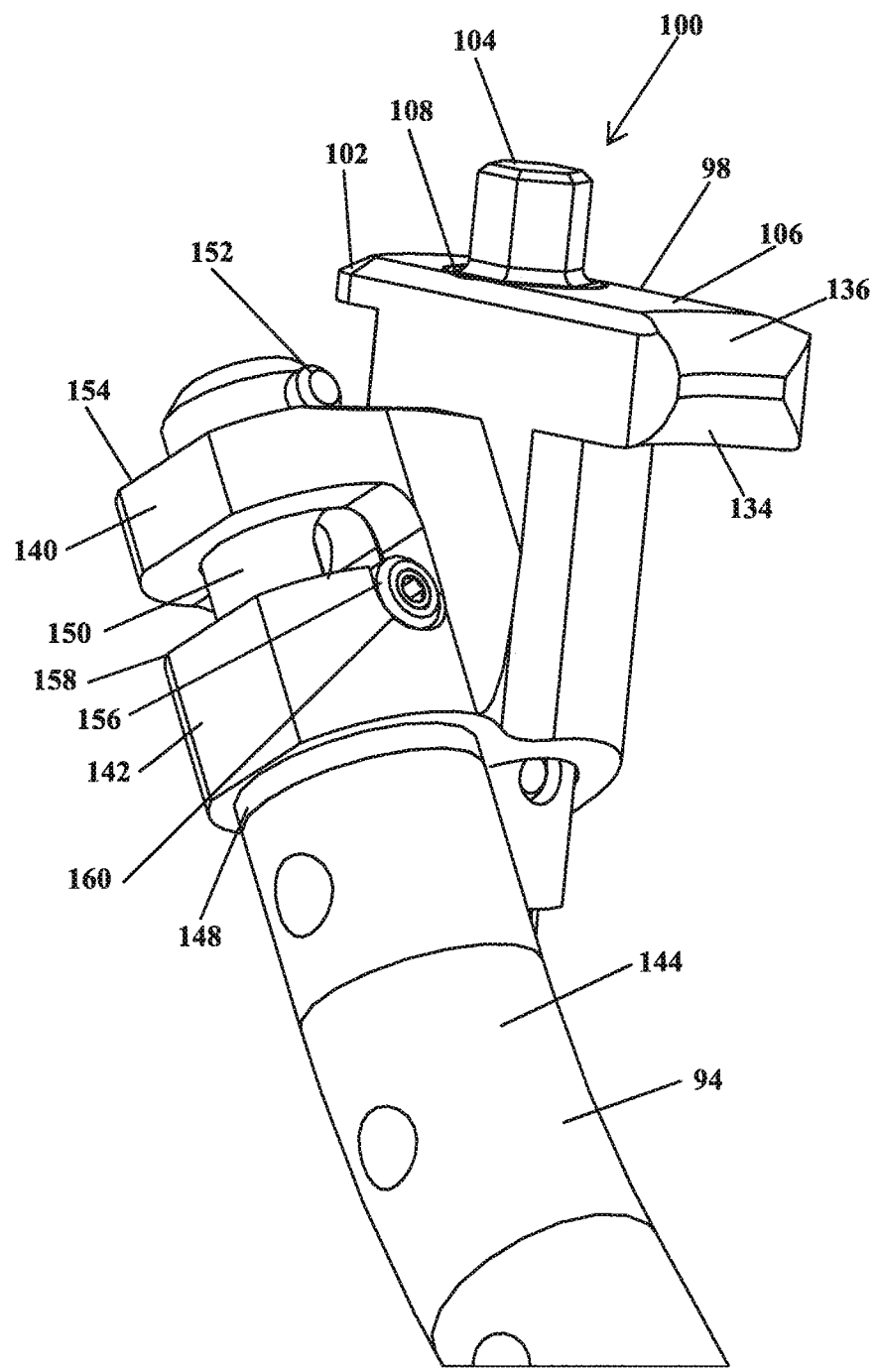
FIG. 13 is an enlarged view of the insertion tool of FIG. 12 showing the implant engaging end.
Figure 14:
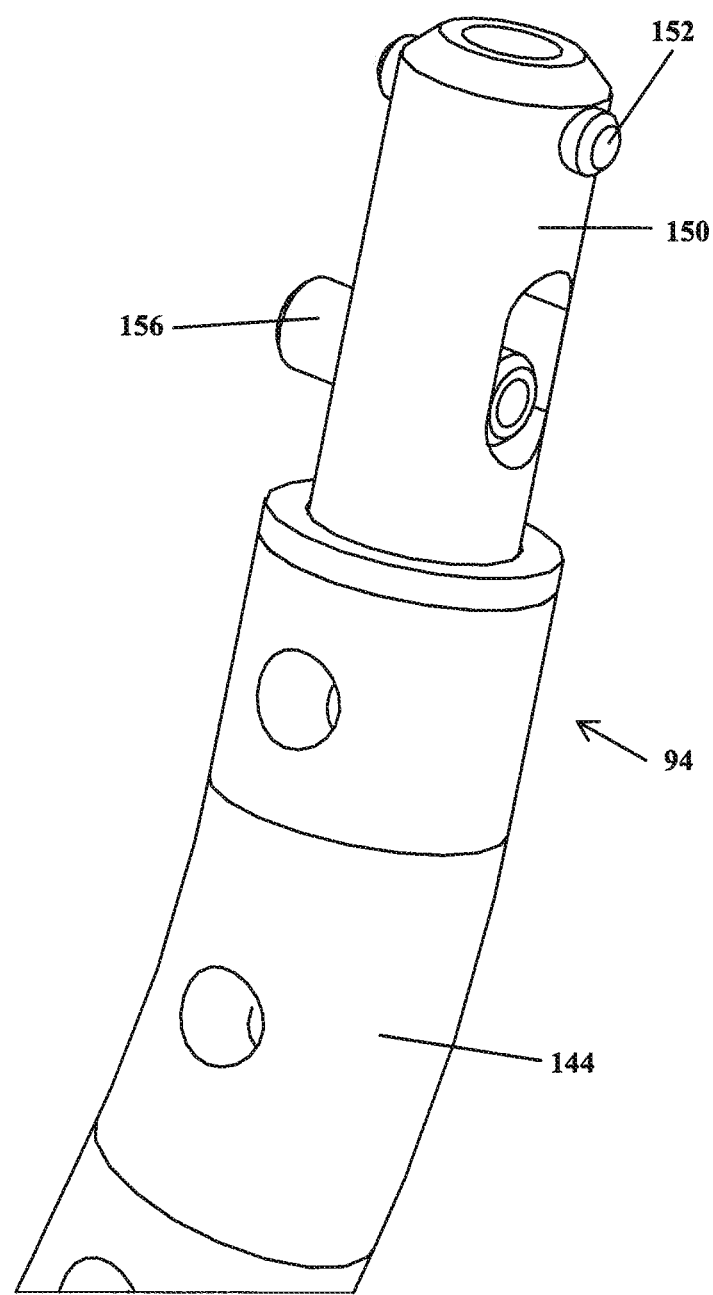
FIG. 14 is an enlarged view of the insertion tool of FIG. 12 showing the distal end of the insertion tool shaft.

As shown in FIGS. 12-14, a flexible inner shaft 150 extends from the handle assembly 92 through rigid sheath 144 and both flanges 140 and 142 of the hook member engagement body 96 and 98. As shown in FIGS. 13 and 14, the inner shaft 150 includes a transverse pin 152 extending therethrough near the distal end 154 of the inner shaft 150. The transverse pin 152 is configured to engage the lower surface 154 of the second flange 142 of the hook member engagement body 96 and 98 to prevent disengagement of the shaft portion 94 and the hook member engagement body 96 and 98.

Figure 15:
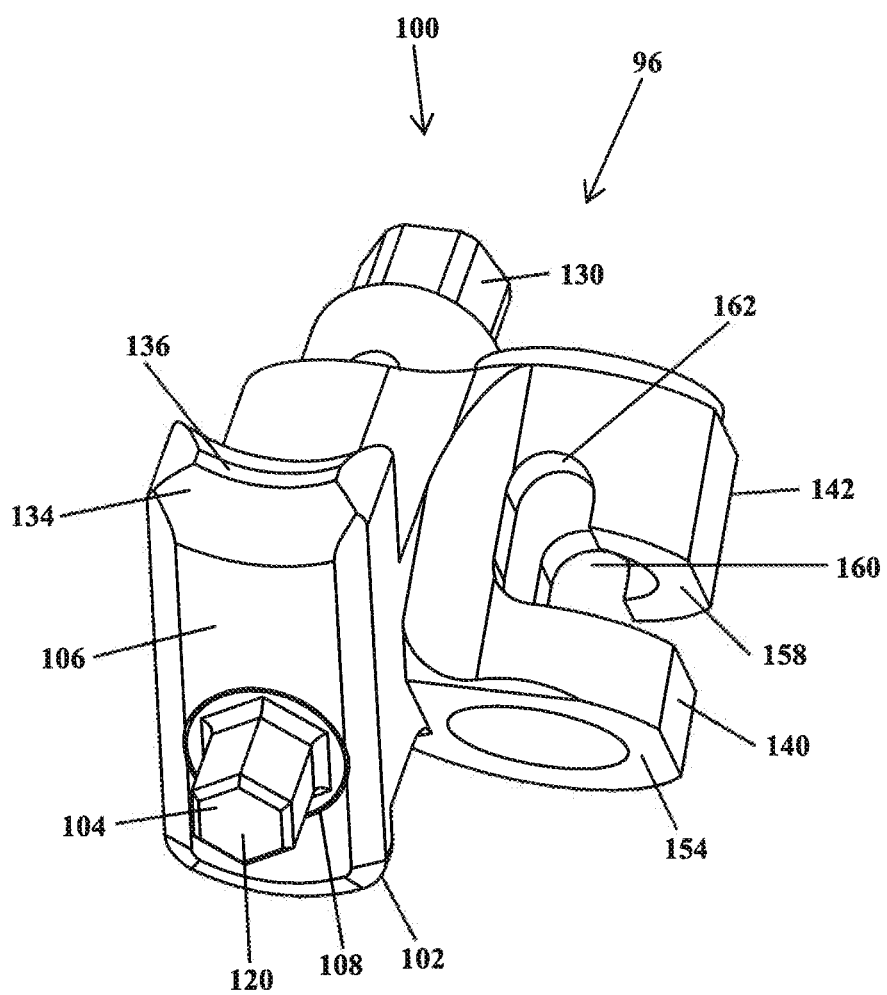
FIG. 15 is a perspective view of the insertion tool of FIG. 12 showing the insertion tool coupler for engaging the lower hook member.
Figure 16:
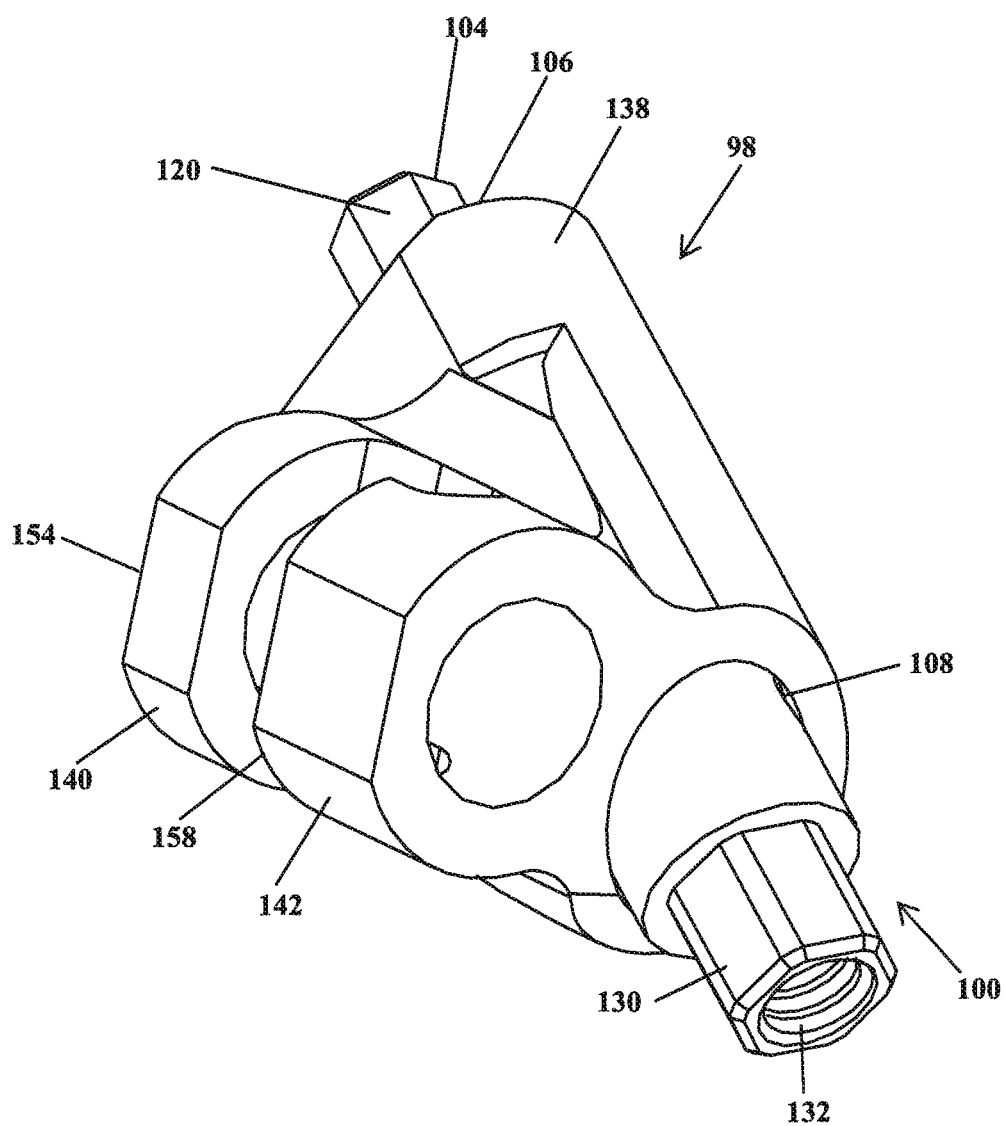
FIG. 16 is an alternative perspective view of the insertion tool of FIG. 12 showing the insertion tool coupler for engaging the upper hook member.
Figure 17:
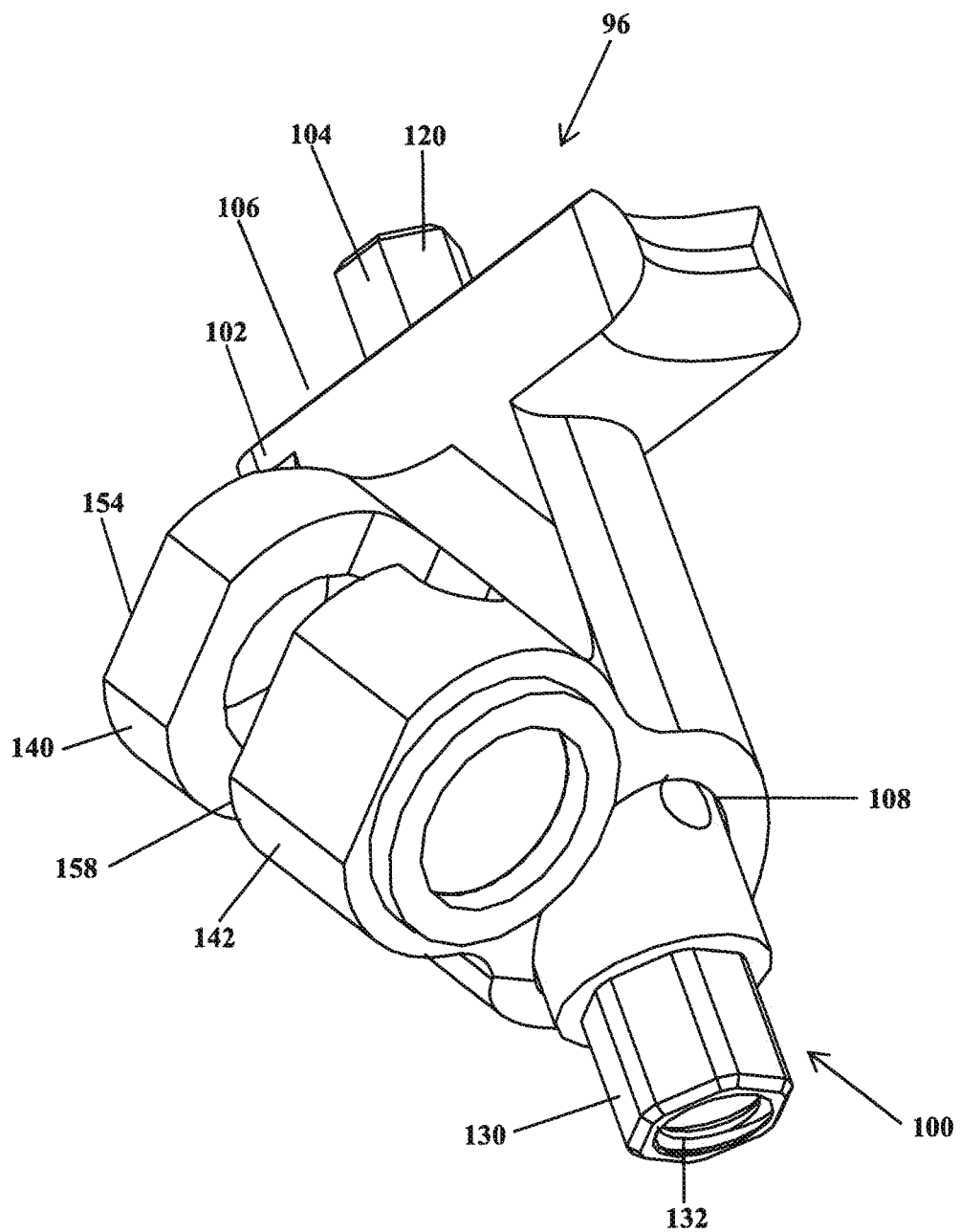
FIG. 17 is a perspective view of the insertion tool of FIG. 12 showing the insertion tool coupler for engaging the lower hook member.
Figure 18:
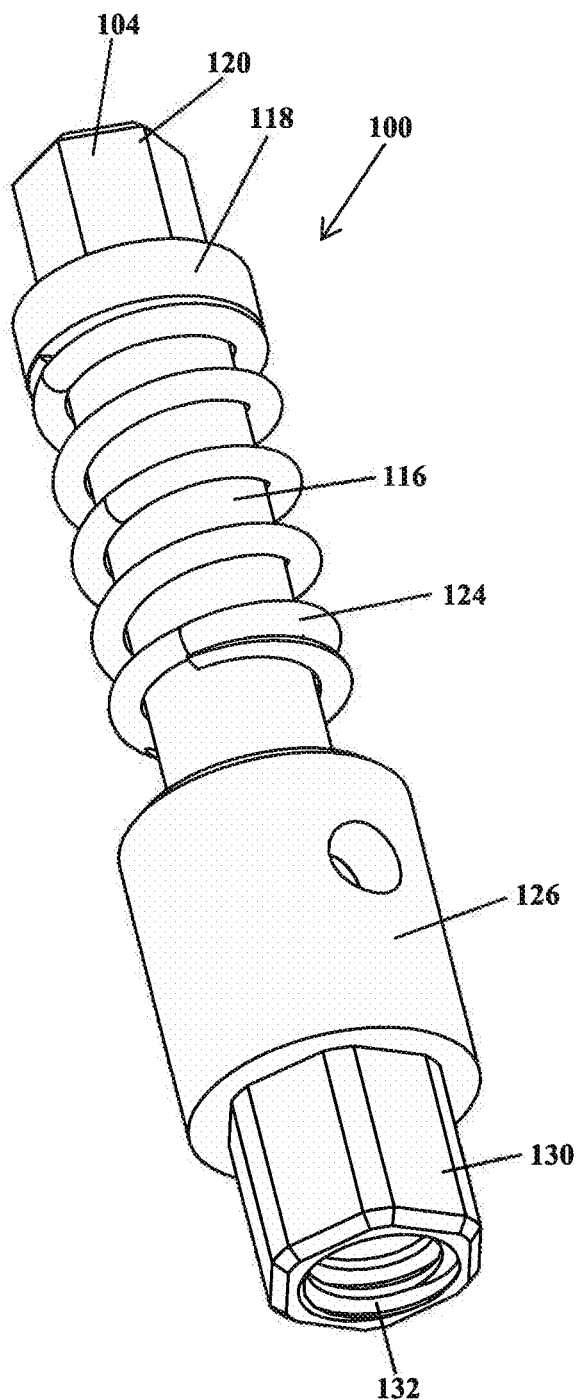
FIG. 18 is a perspective view of the set screw engagement assembly of the insertion tool of FIG. 12.

The inner shaft 150 further includes a position locking pin 156 extending outwardly in one direction from the inner shaft 150. In particular, the position locking pin 156 is configured to be located between the flanges 140 and 142 of the hook member engagement body 96 and 98. As shown in FIGS. 13 and 15, an inner surface 158 of the first flange 154 includes a pair of recesses 160 and 162 sized to receive the position locking pin 156. The insertion orientation 164 of the shaft portions 94 includes the position locking pin 156 within the first recess 160, while the final orientation 166 of the shaft portions 94 includes the position locking pin 156 within the second recess 162 such that the shaft assemblies 94 and handle assemblies 92 are positioned away from the implantation site to provide a clear line of site to the implanted implant device 2.

As shown in FIG. 12, the handle assembly 92 includes a body 168 having an opening 170 extending therethrough sized to receive the flexible inner shaft 150 of the shaft assembly 94. An end of the flexible inner shaft 150 is connected to a depressible mechanism 172 of the handle assembly 94 such that, as the depressible mechanism 172 is depressed, the flexible inner shaft 150 is advanced through the rigid sheath 144 a distance sufficient to remove the position locking pin 156 from the first recess 160 of the primary flange 140. With the depressible mechanism 172 depressed, the handle assembly 94 and shaft assembly 92 can be rotated so that the position locking pin 156 rotates relative to the flanges 140 and 142 of the hook member engaging body 96 and 98 until the position locking pin 156 is adjacent the second recess 162, at which point the depressible mechanism 172 can be released. Upon being released, the flexible inner shaft 150 is retracted through the rigid sheath 144 so that the position locking pin 156 is firmly received in the second recess 162. As a result, the insertion tool 84 is oriented in its final position 166 so that the set screw tightening assemblies 100 can be engaged.

Figure 20:
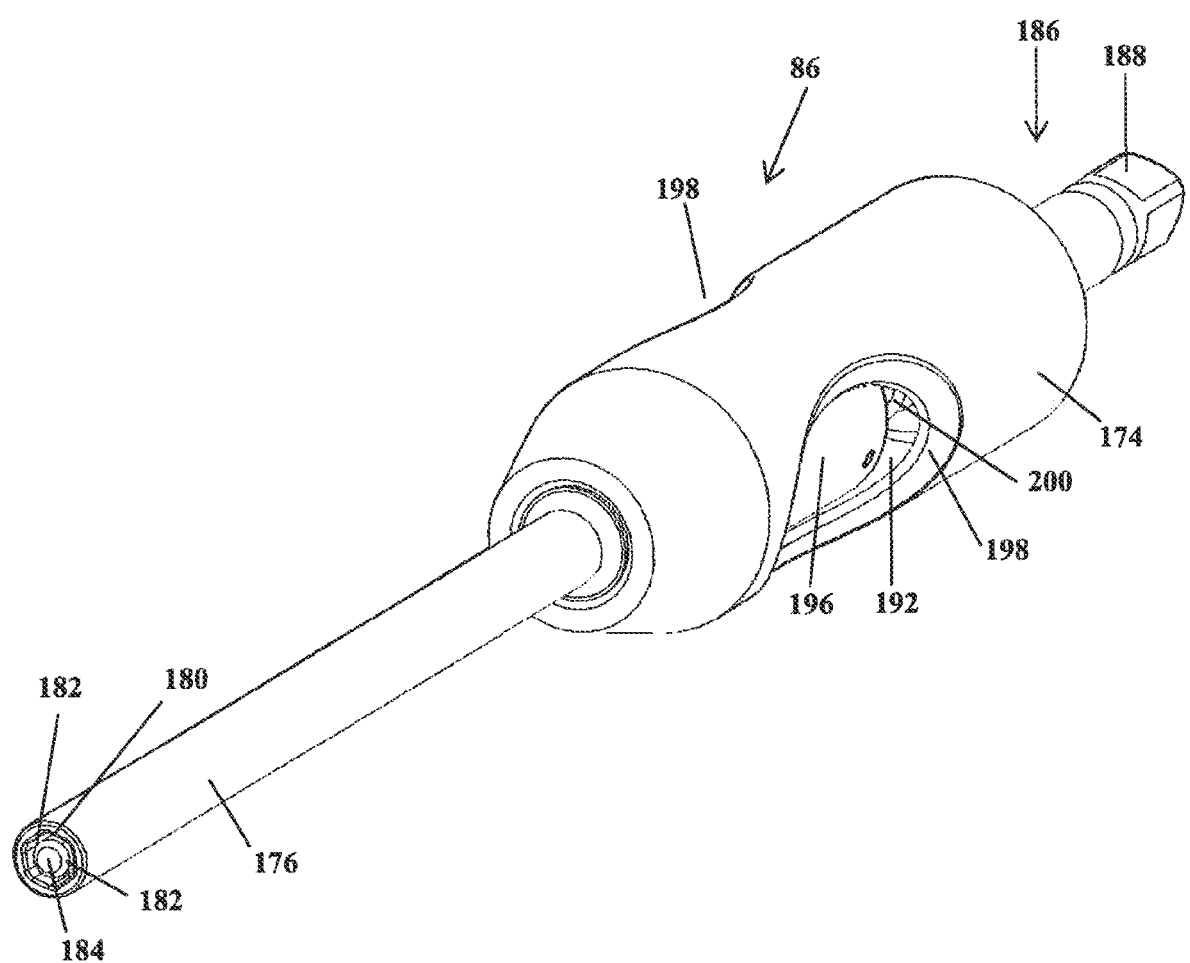
FIG. 20 is a perspective view of the hex drive tool for engaging the set screw engagement assembly of the insertion tool of FIG. 12.
Figure 21:
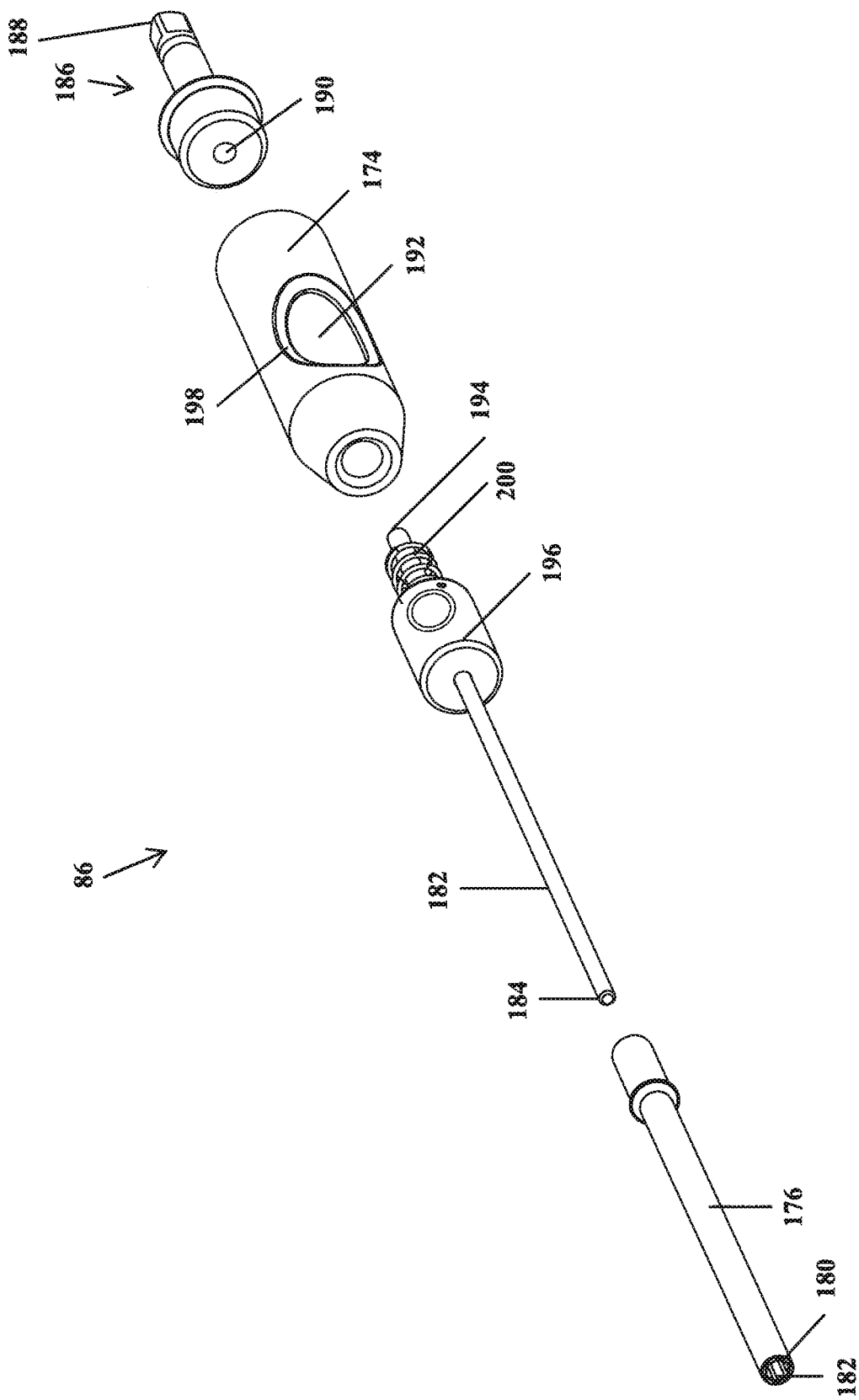
FIG. 21 is an exploded perspective view of the hex drive tool of FIG. 20.
Figure 22:
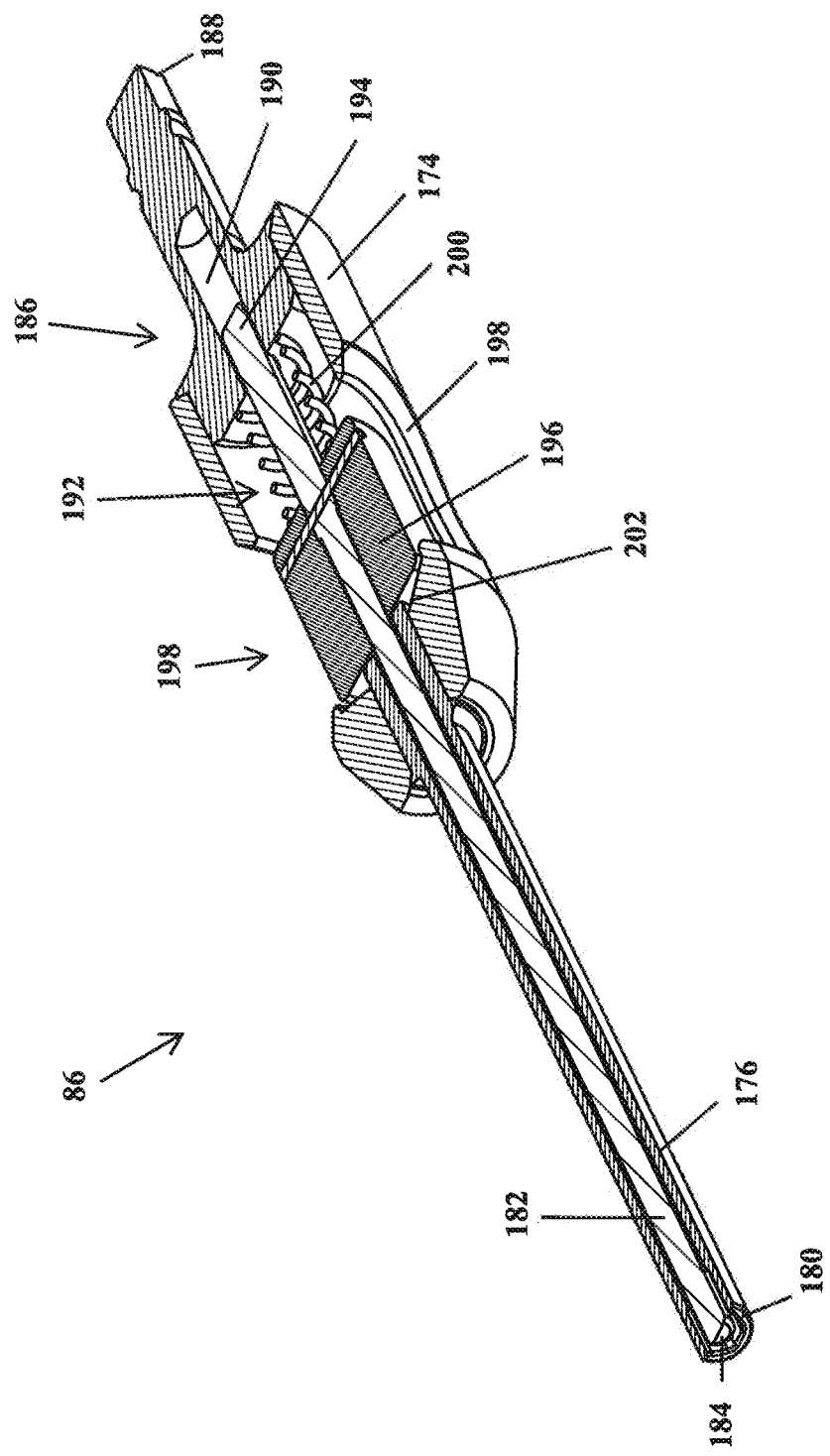
FIG. 22 is a cross section perspective view of the hex drive tool of FIG. 20.

The hex driver tool, as shown in FIGS. 20-22, includes a gripping handle 174 with an outwardly extending elongate hollow shaft 176. A distal end 178 of the elongate hollow shaft 176 has an inner surface 180 configured to correspond to and mate with the outer tool engagement surface 130 of the set screw tightening assembly 100. As shown in FIGS. 20 and 21, the hollow shaft inner surface 180 has six flat surfaces providing a hexagonal opening. When connected to the screw tightening assembly 100, the set screw 40 and 68 can be secured against the elongate guide member 7 by rotating the gripping handle 174 of the hex driver tool 86, which causes the set screw tightening assembly 100 and the set screw 40 and 68 engaged by the set screw tightening assembly 100 to rotate.

As shown in FIGS. 20-22, the hex driver tool 86 further includes a threaded inner shaft 182 extending through the elongate hollow shaft 176 and the gripping handle 174. The threaded inner shaft 182 includes a threaded distal end 184 configured to correspond to and engage the threaded opening 132 of the set screw tightening assembly 100. As shown in FIG. 20, a tool engagement end 186 extends from the gripping handle 174 in a direction opposite the elongate shaft 176. A squared-off end 188 of the tool engagement end 186 is configured to be engaged by a T-Bar to provide quick rotation of the hex driver tool 86. Further, the tool engagement end 186 includes an inner bore 190 extending from a hollow interior 192 of the gripping handle 174 for receiving a proximal end 194 of the threaded shaft 182. As shown in FIG. 22, the threaded shaft 182 includes an oversized portion 196 positioned within the gripping handle 174 for being engaged to rotate the threaded shaft 182. The gripping handle 174 can include windows or opening 198 to provide access to the oversized portion 196.

A spring member 200 is positioned about the threaded shaft 182 between the oversized portion 196 and the tool engagement end 186. The spring member 200 is configured to bias the threaded shaft 182 away from the tool engagement end 186 so that the distal end 184 of the threaded shaft 182 is biased into engagement with the threaded bore 132 of the set screw tightening assembly 100. An inner surface 202 of the hollow gripping handle 174 limits the translation of the threaded shaft 182.

When the threaded shaft 182 first engages the threaded bore 132 of the set screw tightening assembly 100, the threaded shaft 182 is pushed toward the tool engagement end 186 and further into the tool engagement end bore 190. The threaded shaft 182 can then be rotated until so that the hex driver tool 86 is securely engaged to the set screw tightening assembly 100. Once the set screw 40 and 68 is tightened, the hex driver tool 75 can be pulled away from the implant device 2. Pulling the hex driver tool 86 away from the implant device 2 causes the set screw tightening assembly 100 to withdraw from engagement from the set screw 40 and 68, thereby allowing the insertion tool 84 to be shifted out of the tool engagement recess 80 of the hook member 4 and 6 and away from the implant device 2.

In another embodiment, the implant device 2 can be installed using a single tool. As shown in FIGS. 25-34, the inferior hook member 6 can include a pair of tool engagement knobs 204 extending from either side thereof adjacent the set screw 68. The knobs 204 are configured to be engaged by the installation tool 206 during installation. Further, adjacent the set screw 68 of the inferior hook member 6, the inferior hook member 6 includes a tool engagement boss 208 which can be engaged by a linkage or hook 210 of the implant installation tool 206. With the arms 8 and 10 of the superior and inferior hooks 4 and 6 engaging the adjacent lamina 302 and 306, cradles 212 of the installation tool 206 engage and maintain the general location of the knobs 204 of the inferior hook member 6 and a linkage 210 connected to a drive rod 214 of the installation tool 206 pulls or draws the tool engagement boss 208 of the inferior hook 6 backward away from the lamina 302 and 306, so as to cause a pivoting of the upper and lower hook members 4 and 6 around the knobs 204 from the compact insertion profile 30 to the implanted configuration 32.

Once in the deployed configuration 32, the upper and lower hook members 4 and 6 can be reoriented opposite to one another, if necessary, to achieve the proper fit with the adjacent lamina 302 and 306. If the implant is to be distracted, a camming handle 216 of the tool 206 can advance a cam 218 to engage a camming surface 220 of the superior hook member 4. The camming handle 216 can rotate the cam 218 and cause the cam 218 to engage the camming surface 220 and shift the superior hook member 4 away from the inferior hook member 6, the inferior hook member 6 remaining engaged by the implantation tool 206 via the knobs 204 extending from either side thereof. Once the superior and inferior hook members 4 and 6 have been distracted to the desired distracted orientation 46, a screw tightening mechanism can be fed through an opening 222 of the tool 206 to engage the set screw 68 of the inferior hook member 4 and tighten the set screw 68 to secure the guide shaft 26 within the guide shaft receiving bore 28 of the inferior hook member 6. An exemplary screw tightening mechanism includes an elongate shaft configured to be received and extend through the tool opening 222 with a screw engagement end configured to engage the screw 60 and 68. The screw tightening mechanism can further includes a squared off end of the elongate shaft opposite the screw engagement end. In one embodiment, the square off end is configured to be engaged by a t-bar tool for providing rotational movement of the screw tightening mechanism. Further, once the superior hook member 4 and inferior hook member 6 have been adjusted via the multi-axial pivot connection 16 therebetween to adjust for the geometries of the adjacent lamina 302 and 306, the set screw 40 of the superior hook member 4 is tightened to insure the upper and lower hook members 4 and 6 remain in the desired configuration relative to one another. The drive rod 214 of the tool 206 can be further withdrawn, causing the linkage 210 to disengage the tool boss 208 of the inferior hook portion 6 and allow the knobs 204 to be freely removed from the installation tool cradles 212. Once completed, the insertion tool 206 is removed and the surgery is completed.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A spinal implant assembly for engaging adjacent vertebrae, the spinal implant assembly comprising:
    an elongate guide device having a shaft portion and a longitudinal axis along which the elongate guide device extends;
    a first hook portion having a first pair of hook arms, a first seat portion between the first pair of hook arms facing a first direction and configured for engaging a first vertebral surface, and an elongate slot opening;
    a second hook portion having a second pair of hook arms and a second seat portion between the second pair of hook arms for facing in a second direction away from the first seat portion generally opposite to the first direction in an implanted orientation of the first and second hook portions and configured for engaging a second vertebral surface;
    a slide connection between the elongate guide device and the second hook portion to allow the second hook portion to translate along the elongate guide device for distraction of the first and second vertebral surfaces; and
    a multi-axial pivot connection between the elongate guide device and the first hook portion to allow the first hook portion to pivot for securely engaging the first vertebral surface despite variations in the relative positions of the first and second vertebral surfaces engaged by the first and second hook portions, respectively, the multi-axial pivot connection including the elongate slot opening of the first hook portion configured to allow the first hook portion to be pivoted at least about 90 degrees relative to the longitudinal axis to a compact, insertion orientation relative to the second hook portion with the shaft portion of the elongate guide device extending and shifting through the slot opening as the first hook portion is pivoted to the compact, insertion orientation.

2. The spinal implant assembly of claim 1 wherein the multi-axial pivot connection comprises a generally spherical end portion of the elongate guide device, and a generally spherical socket portion of a first hook portion in which the generally spherical end portion is received; and
    the shaft portion of the elongate guide device connected to the generally spherical end portion to extend away from the generally spherical socket portion for translation of the second hook portion therealong toward and away from the first hook portion.

3. The spinal implant assembly of claim 1 wherein the second hook portion and the elongate guide device have a detachable connection therebetween.

4. The spinal implant assembly of claim 3 wherein the detachable connection comprises a snap-fit connection between the second hook portion and the elongate guide device.

5. The spinal implant assembly of claim 1 wherein the slide connection includes the shaft of the elongate guide device and a bore of the second hook portion for receiving the shaft therein along which the second hook portion can translate for distracting the vertebrae with the elongate guide device generally aligned with the seat portions of the first and second hook members.

6. The spinal implant assembly of claim 1 wherein the elongate guide device includes a motion limiting protrusion at one end thereof to stop and limit translation of the second hook portion in a distraction direction away from the first hook portion.

7. The spinal implant assembly of claim 6 wherein the shaft of the elongate guide device includes tapered sides and the motion limiting protrusion is formed at distal ends of the tapered sides.

8. The spinal implant assembly of claim 1 wherein the multi-axial pivot connection is a universal pivot connection.

9. A spinal implant assembly for engaging respective laminae of adjacent vertebrae, the spinal implant assembly comprising:
    a pair of hook members each having a body including a seat portion for engaging adjacent laminae and a longitudinal axis along which the body extends;
    an elongate guide device for being connected to the hook members and having a longitudinal axis thereof;
    a pivot connection between one of the hook members and the elongate guide device for shifting between a compact insertion orientation and a compact implanted orientation with the compact insertion orientation having the one hook member pivoted so that the one hook member longitudinal axis extends generally transverse to the elongate guide device longitudinal axis, and the compact implanted orientation having the one hook member pivoted so that the one hook member longitudinal axis is generally parallel with the elongate guide device longitudinal axis for orienting the seat portions of the hook members to face in generally opposite directions away from one another so that the seat portions can engage the adjacent laminae, the pivot connection configured to permit the one hook member to pivot at least about 90 degrees relative to the longitudinal axis; and a slide connection between the other hook member and the elongate guide device to allow the other hook member to translate along the elongate guide device between the compact implanted orientation and an extended implanted orientation with the hook members spaced from each other and the respective seats thereof engaged with the adjacent laminae to distract the vertebrae.

10. The spinal implant assembly of claim 9 wherein the other hook member and the elongate guide device have a detachable connection therebetween.

11. The spinal implant assembly of claim 10 wherein the detachable connection comprises a snap-fit connection between the other hook member and the elongate guide device.

12. The spinal implant assembly of claim 9 wherein the elongate guide device comprises a shaft having opposite ends with the slide connection comprising a bore of the one hook member in which the shaft is slideably received, the pivot connection comprising a curved surface of one of the shaft ends and a cooperating curved recess of the one hook member in which the one shaft end is received, and a radially enlarged portion at the other end of the shaft for limiting the spacing of the hook members from each other in the extended implanted orientation.

13. The spinal implant assembly of claim 12 wherein the other hook member and the shaft of the elongate guide device have a detachable, snap-fit connection therebetween comprising a resilient portion of the other hook member and cam surfaces of the radially enlarged portion of the shaft for camming against and resiliently deforming the resilient portion when the other hook member is connected to and disconnected from the shaft.

14. The spinal implant assembly of claim 9 wherein the longitudinal axis of the elongate hook member body extends obliquely to the longitudinal axis of the elongate guide device in the compact insertion orientation.

15. The spinal implant assembly of claim 9 wherein the pivot connection is a multi-axial pivot connection.

16. The spinal implant assembly of claim 9 wherein the pivot connection is a universal pivot connection.

17. The spinal implant assembly of claim 9 wherein the hook members include tool engagement recessed pockets for being engaged by an insertion tool.

18. The spinal implant assembly of claim 9 wherein the longitudinal axes of the hook member bodies extend transversely to one another with the hook members in the compact insertion orientation.

19. A spinal implant assembly for distracting adjacent vertebrae, the spinal implant assembly comprising:

an elongate guide device having a shaft and a longitudinal axis;

a first hook device having a first pair of hook arms and a first seat therebetween with the seat configured to engage a laminar surface of a first one of the adjacent vertebrae;

a second hook device having a second pair of hook arms and a second seat therebetween with the seat configured to engage a laminar surface of a second one of the adjacent vertebrae;

a first connection between the first hook device and the elongate guide device;

a second connection between the second hook device and the elongate guide device configured to allow the second hook device to translate along the elongate guide device to orient the first and second hook devices in operative positions relative to each other engaged with the respective laminar surfaces for distracting the first and second vertebrae, the first and second connections being configured such that with the first and second hook devices in the operative positions, the longitudinal axis of the elongate guide device extends through the seat or one of the arms of each of the first and second hook devices so that the elongate guide device is compactly arranged to extend in the space between the laminar surfaces engaged by the hook device seats, the second connection including a bore positioned between the second pair of hook arms at the seat of the second hook device whereby the shaft of the elongate guide device is received in the bore to allow the second hook device to translate linearly along the shaft toward and away from the first hook device.

20. The spinal implant assembly of claim 19 wherein the first connection is a pivot connection and the second connection is a slide connection.

21. A spinal implant assembly for distracting adjacent vertebrae, the spinal implant assembly comprising:

an elongate guide device including a shaft;

a first hook device having a first pair of hook arms, a first seat portion between the first pair of hook arms for facing a first direction and configured for engaging a first vertebral surface, and an elongate slot opening;

a first connection between the first hook device and the elongate guide device, the first connection including the elongate slot opening of the first hook device to allow the first hook device to be pivoted to a compact, insertion orientation with the shaft portion of the elongate guide device extending and shifting through the slot opening as the first hook device is pivoted to the compact, insertion orientation;

a second hook device having a second pair of hook arms and a second seat portion between the second pair of hook arms for facing away from the first seat portion in a second direction generally opposite the first direction in an implanted orientation of the first and second hook portions and configured for engaging a second vertebral surface; and a second releasable connection between the second hook device and the elongate guide device configured to allow the second hook device to be pulled in the second direction to remove the second hook device from the elongate guide device and to be pushed in the first direction to connect the second hook device to the elongate guide device, the second releasable connection including a bore opening to the seat of the second hook device whereby the shaft of the elongate guide device is received in the bore to allow the second hook device to translate linearly along the shaft in the first and second directions.

22. The spinal implant assembly of claim 21 wherein the second connection between the second hook device and the elongate guide device comprises a snap-fit connection.

23. The spinal implant assembly of claim 21 wherein the second connection between the second hook device and the elongate guide device comprises a slide connection to allow the second hook device to translate along the elongate guide device for distracting the first and second vertebral surfaces.

24. The spinal implant assembly of claim 21 wherein the first connection comprises a pivot connection to allow the first hook device to pivot for securely engaging the first vertebral surface despite variations in the relative positions of the first and second vertebral surfaces engaged by the seats of the first and second hook devices, respectively.

* * * * *